(12) United States Patent
Schulman et al.

(10) Patent No.: US 7,778,679 B2
(45) Date of Patent: Aug. 17, 2010

(54) IMPLANTABLE SENSOR AND INTEGRITY TESTS THEREFOR

(75) Inventors: Joseph H. Schulman, Santa Clara, CA (US); Rajiv Shah, Rancho Palos Verdes, CA (US); John C. Gord, Venice, CA (US); Lyle D. Canfield, Lake Hughes, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 2594 days.

(21) Appl. No.: 10/000,977

(22) Filed: Nov. 30, 2001

(65) Prior Publication Data

US 2002/0042561 A1    Apr. 11, 2002

Related U.S. Application Data

(60) Continuation of application No. 09/360,343, filed on Jul. 22, 1999, now Pat. No. 6,387,048, and a division of application No. 08/954,171, filed on Oct. 20, 1997, now Pat. No. 6,088,608.

(51) Int. Cl.
*A61B 5/05* (2006.01)
*A61B 5/00* (2006.01)
*A61N 1/00* (2006.01)
*H02M 7/217* (2006.01)
*G01R 19/22* (2006.01)

(52) U.S. Cl. .................. 600/345; 600/309; 607/2; 327/104; 363/127

(58) Field of Classification Search ............... 600/300, 600/301, 345–366, 309; 363/671.08, 125, 363/127, 131; 257/119
See application file for complete search history.

(56) References Cited

U.S. PATENT DOCUMENTS

| | | | |
|---|---|---|---|
| 3,434,034 A | 3/1969 | Garber et al. | 321/43 |
| 3,757,770 A | 9/1973 | Brayshaw et al. | 128/2 R |
| 4,086,624 A | 4/1978 | Fraley | 307/127 |
| 4,094,308 A * | 6/1978 | Cormier | 600/528 |
| 4,186,749 A * | 2/1980 | Fryer | 600/561 |
| 4,289,141 A * | 9/1981 | Cormier | 600/526 |
| 4,349,769 A | 9/1982 | Willoteaux | 318/677 |
| 4,431,004 A | 2/1984 | Bessman et al. | 128/635 |
| 4,484,987 A | 11/1984 | Gough | 204/1 T |

(Continued)

FOREIGN PATENT DOCUMENTS

EP    0 232 451    8/1987

(Continued)

OTHER PUBLICATIONS

Gough, et al.; "Two-Dimensional Enzyme Electrode Sensor for glucose", Analytical Chemistry, vol. 57, No. 12, pp. 2351-2357 (1985).

(Continued)

*Primary Examiner*—Charles A Marmor, II
*Assistant Examiner*—Navin Natnithithadha
(74) *Attorney, Agent, or Firm*—Foley & Lardner LLP

(57) ABSTRACT

An implantable sensor includes electronic circuitry for automatically performing on a periodic basis, e.g., every 1 to 24 hours, specified integrity tests which verify proper operation of the sensor.

61 Claims, 10 Drawing Sheets

U.S. PATENT DOCUMENTS

| | | | | |
|---|---|---|---|---|
| 4,507,525 | A | 3/1985 | Siligoni et al. | 179/70 |
| 4,535,203 | A | 8/1985 | Jenkins et al. | 179/81 R |
| 4,627,906 | A | 12/1986 | Gough | 204/415 |
| 4,671,288 | A | 6/1987 | Gough | 128/635 |
| 4,703,756 | A | 11/1987 | Gough et al. | 123/635 |
| 4,704,545 | A | 11/1987 | Tanaka et al. | 307/236 |
| 4,759,828 | A | 7/1988 | Young et al. | 204/1 T |
| 4,781,798 | A | 11/1988 | Gough | 204/1 E |
| 4,890,620 | A | 1/1990 | Gough | 128/635 |
| 4,942,401 | A | 7/1990 | Gessaman et al. | 341/157 |
| 5,165,407 | A | 11/1992 | Wilson et al. | 128/635 |
| 5,174,291 | A | 12/1992 | Schoonen et al. | 128/632 |
| 5,372,133 | A | 12/1994 | Hogen Esch | 128/631 |
| 5,411,528 | A | 5/1995 | Miller et al. | 128/419 D |
| 5,412,556 | A * | 5/1995 | Marinus | 363/21.05 |
| 5,497,772 | A | 3/1996 | Schulman et al. | 128/635 |
| 5,510,972 | A | 4/1996 | Wong | 363/127 |
| 5,540,729 | A | 7/1996 | Weijand | 607/35 |
| 5,691,658 | A | 11/1997 | Klein | 327/104 |
| 5,755,743 | A | 5/1998 | Volz et al. | 607/37 |
| 5,776,324 | A | 7/1998 | Usala | 204/403 |
| 5,825,214 | A | 10/1998 | Klosa | 327/104 |
| 5,917,346 | A * | 6/1999 | Gord | 327/101 |
| 5,999,848 | A * | 12/1999 | Gord et al. | 607/2 |
| 5,999,849 | A * | 12/1999 | Gord et al. | 607/2 |
| 6,088,608 | A * | 7/2000 | Schulman et al. | 600/345 |

FOREIGN PATENT DOCUMENTS

| | | |
|---|---|---|
| EP | 0 670 499 A1 | 9/1995 |
| EP | 0 791 706 A1 | 8/1997 |
| WO | WO 89/05058 | 6/1989 |
| WO | WO 97/24795 | 7/1997 |

OTHER PUBLICATIONS

US Notice of Allowance for U.S. Appl. No. 08/954,171 dated Aug. 13, 1999.
US Notice of Allowance for U.S. Appl. No. 09/360,343 dated Jan. 2, 2001.
US Office Action for U.S. Appl. No. 08/954,171 dated Jun. 18, 1999.
US Office Action for U.S. Appl. No. 09/360,343 dated Sep. 12, 2000.

* cited by examiner

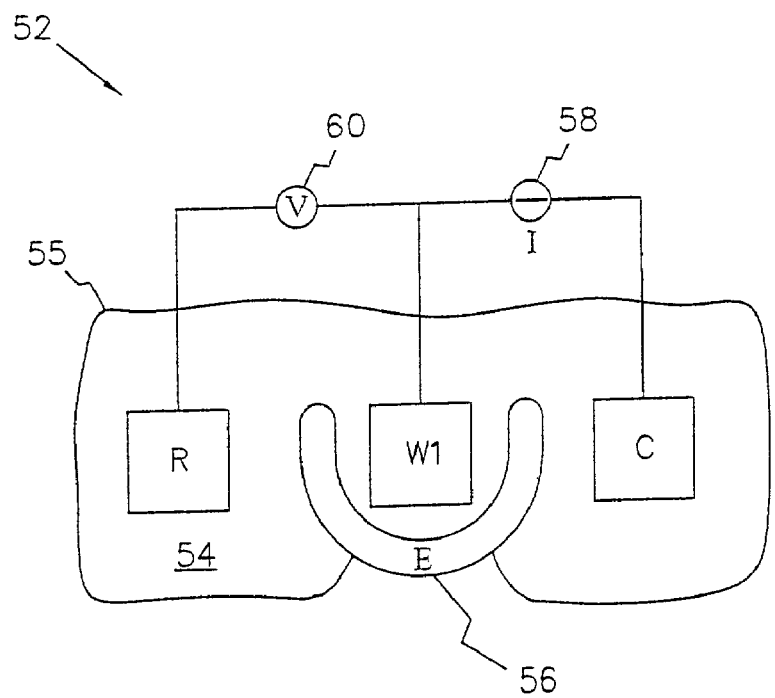
FIG. 2A
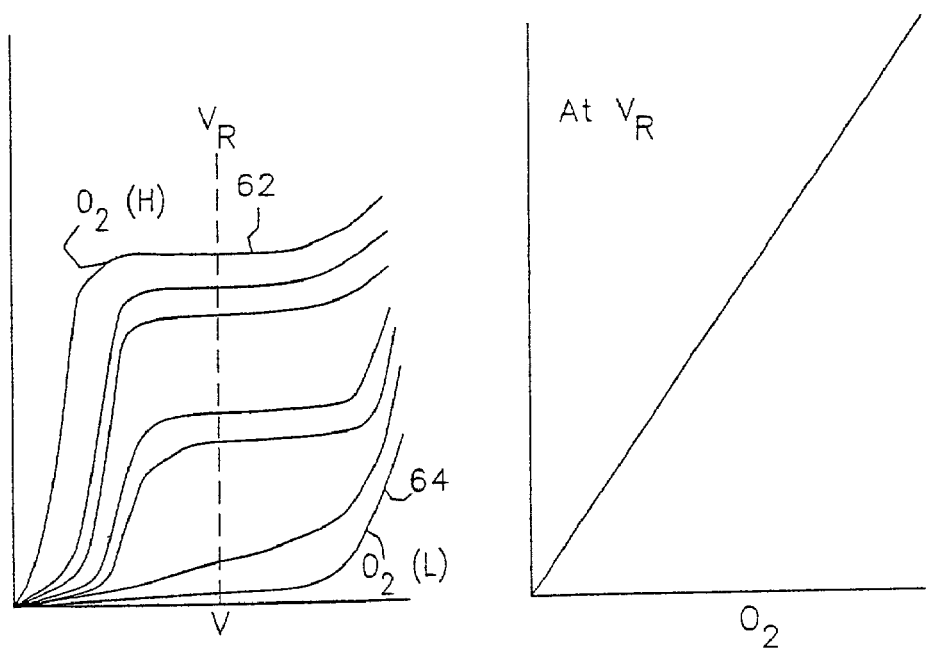
FIG. 2B
FIG. 2C

US 7,778,679 B2

IMPLANTABLE SENSOR AND INTEGRITY TESTS THEREFOR

This application is a Continuation of application Ser. No. 09/360,343, filed Jul. 22, 1999, which is a Divisional of Ser. No. 08/954,171, filed Oct. 20, 1997.

BACKGROUND OF THE INVENTION

The present invention relates to implantable sensors, and more particularly to monitoring such sensors for proper performance. Even more particularly, the present invention relates to integrity tests that are performed on a regular basis in order to confirm proper sensor operation. A preferred sensor with which the present invention may be used is an implantable glucose sensor.

Implantable sensors are sensors adapted to be implanted within living tissue, e.g., within a living patient. The patient may comprise an animal or a human. Such implantable sensors are typically used to monitor one or more physiological parameters associated with the patient. For example, an implantable sensor may monitor a patient's blood or other body fluids for the presence or absence of a specific substance. Other implantable sensors may monitor the patient's body temperature. While a preferred sensor for use with the present invention comprises an implantable glucose sensor, or groups of glucose sensors, it is to be understood that the invention may be used with any type of implantable sensor(s). It is also to be understood that the principles underlying operation of an implantable sensor apply equally well to any sensor that is to remain unattended and submerged or immersed within a hostile environment, e.g., within a saline solution such as seawater, for a prolonged period of time. Thus, although the sensors described herein find particular applicability to sensors adapted to be implanted within living tissue, and the description is directed to such implantable sensors, the invention may also be applied to remote sensors of any kind that must be immersed unattended in a hostile environment for long periods of time.

In general, an implantable sensor may be used to provide valuable data that assists in diagnosing or treating an illness, or to help maintain or sustain a given level of physiological, chemical, or other activity or inactivity. In the case of glucose sensors, which are typically used with some type of insulin-delivery system in order to treat diabetics, the glucose sensors provide invaluable data needed to maintain the concentration of glucose within the patient at an acceptable level. Such glucose sensors must perform properly; otherwise, false data may be provided. Such false data (if acted upon) could result in the administration of an inappropriate amount of insulin, leading to death or serious injury. There is thus a critical need in the art for a sensor which is reliable and which can be monitored for proper function on a regular basis. Likewise, there is a need for a glucose sensor which must work properly within certain specific limits of accuracy.

SUMMARY OF THE INVENTION

The above and other needs are addressed by the present invention which comprises an implantable sensor that includes integral means for automatically performing a series of integrity tests that test the sensor for proper performance, and which thereby ensure that the sensor is correctly and accurately performing its intended monitoring function(s).

In accordance with one embodiment of the invention, an electrochemical sensor is provided that has an hermetically sealed portion and a non-hermetically sealed portion. The hermetically sealed portion contains electronic circuitry; and the non-hermetically sealed portion has at least one electrode associated therewith. The electronic circuitry includes means for measuring a specified parameter within body fluids or tissue to which the at least one electrode is exposed, and means for performing at least one integrity test to verify proper operation of the sensor. Preferably, the means for performing the integrity test comprises means for automatically performing the integrity test upon occurrence of a specified event, such as the passage of time in accordance with a prescribed schedule (e.g., once every hour, or once every day), or the sensing of a parameter that is out of tolerance.

A preferred embodiment of the invention comprises an implantable glucose sensor. Such glucose sensor includes, inter alia, electronic circuitry for automatically performing on a periodic basis, e.g., every 1 to 24 hours, specified integrity tests which verify the proper operation of the glucose sensor. The basic structure and operating characteristics of a preferred implantable glucose sensor adapted for use with the present invention are described generally in U.S. Pat. No. 5,497,772, incorporated herein by reference. Important features and enhancements of such sensor are further described in U.S. patent application Ser. No. 08/928,867 (Now U.S. Pat. No. 5,999,848), U.S. patent application Ser. No. 08/928,868 (Now U.S. Pat. No. 5,917,346), U.S. patent application Ser. No. 08/928,871 (Now U.S. Pat. No. 5,999,849), U.S. patent application Ser. No. 08/945,166, filed concurrently herewith (Now U.S. Pat. No. 6,119,028), and U.S. patent application Ser. No. 08/953,817, filed concurrently herewith (Now U.S. Pat. No. 6,081,736), all of which are assigned to the same assignee as the present application, and all of which patent applications are also incorporated herein by reference.

The preferred glucose sensor is adapted for insertion into the venous system of a patient where it is exposed to the patient's blood, or into other areas of the patient where it is exposed to other tissue or fluids of the patient. Once implanted, the sensor produces electrical signals, i.e., an electrical current, that is related to the sensed glucose concentration.

Most implantable sensors have one or more electrodes adapted to contact the body tissue or fluids within which the sensor is implanted. It is through such electrodes that the sensor is able to sense the particular parameter it is designed to sense.

For example, as described in the above-referenced patent and patent applications, the preferred glucose sensor includes several electrodes, e.g., two working electrodes (W1 and W2), at least one reference electrode (REF1), and a counter electrode (CNTR). Some of the electrodes, e.g., the working electrodes and the counter electrode, are made or coated from platinum, while the reference electrode is typically made from or coated with silver chloride. Some of the electrodes are surrounded by a prescribed enzyme, typically in the form of a gel. A preferred enzyme used for this purpose is glucose oxidase (referred to herein as "GOX"). All of the electrodes are further submersed in a suitable conductive fluid, e.g., a saline solution.

The electrodes of the preferred glucose sensor are typically formed on one side of a substrate, with membranes being formed to confine the conductive fluid and/or GOX in the areas needed to expose the electrodes. On the other side of the substrate, electronic circuitry is formed that connects the electrodes appropriately so that the desired electrochemical activity can be monitored and used as a measure of the concentration of glucose to which the sensor is exposed. Such circuitry includes not only circuits that monitor the sensed glucose concentration (which is done, as explained below, by monitoring the current flow between the electrodes, which provides a measure of the oxygen concentration, which oxygen concentration in the presence of an enzyme is inversely proportional to the concentration of glucose), but also includes data processing circuitry to preliminary process the sensed data (e.g., the measured current) and transmit it over a two-line connection cable with a controller circuit to which the sensor is connected. The circuitry is hermetically sealed, and non-exposed portions of the electrodes are similarly sealed under a coating of aluminum oxide or alumina or other suitable insulator. Portions of the sensor are also insulated in epoxy. In a preferred embodiment, several, e.g., three, such sensors may be daisy-chained together, each operating independently of the others, yet each being in close proximity with the others so that measured data from different ones of the sensors can be compared.

In order for the sensor to perform its intended function, it is important that the electrodes and circuitry all operate as designed, and that the various insulative material or coatings used with the sensor, e.g., alumina, zerconia, wax and/or epoxy, provide the needed insulation and/or sealing properties.

In accordance with one aspect of the invention, special test circuitry is provided as part of the sensor circuitry to periodically check the integrity of the critical sensor functions and/or parameters. When necessary or desired, the results of the integrity tests are then reported by generating appropriate data signals that provide an indication of the results of such integrity tests, e.g., that warn when a given test has failed, and/or that provide test data from which a quantitative measure of the test results can be obtained.

In a preferred configuration, a plurality of sensors, e.g., three sensors, are daisy-chained together and implanted within a patient in the same general area, i.e., in the same tissue or body fluids. Each sensor operates independently of the others. If all the sensors are functioning properly, then the output data obtained from each sensor should be approximately the same. The data sensed by each sensor may thus be used as a crosscheck against the data sensed by the other sensors. In a similar manner, the information obtained from the periodic integrity tests may be regularly compared and checked with the corresponding integrity test information obtained from the other sensors of the same group of chained-together sensors. In this manner, the overall integrity of the integrity tests is itself checked periodically.

It is thus an object of the invention to provide, within an implantable sensor, e.g., of the general type disclosed in U.S. Pat. No. 5,497,772, or a similar implantable electrochemical sensor, a means for automatically verifying the integrity of the sensor on a periodic basis.

It is a feature of the invention to provide electrical/electronic circuits included as part of the sensor circuitry that carry out a series of integrity tests on the sensor on a scheduled basis, and that report the results of such tests by way of test data that can be monitored over time and/or compared with similar test data obtained from other implanted sensors.

BRIEF DESCRIPTION OF THE DRAWINGS

The above and other aspects, features and advantages of the present invention will be more apparent from the following more particular description thereof, presented in conjunction with the following drawings and Appendix wherein:

FIG. 2A is an electrical diagram of a simplified glucose sensor;

FIG. 2B is a graph that qualitatively depicts the relationship between electrical current delivered to the electrodes of the glucose sensor of FIG. 2A and the voltage applied between the electrodes, and how such relationship varies as a function of oxygen content;

FIG. 2C is a graph that qualitatively depicts the approximately linear relationship that exists at a fixed electrode voltage between the electrical current passing through the electrode of the glucose sensor of FIG. 2A and the oxygen concentration;

Figure 1:
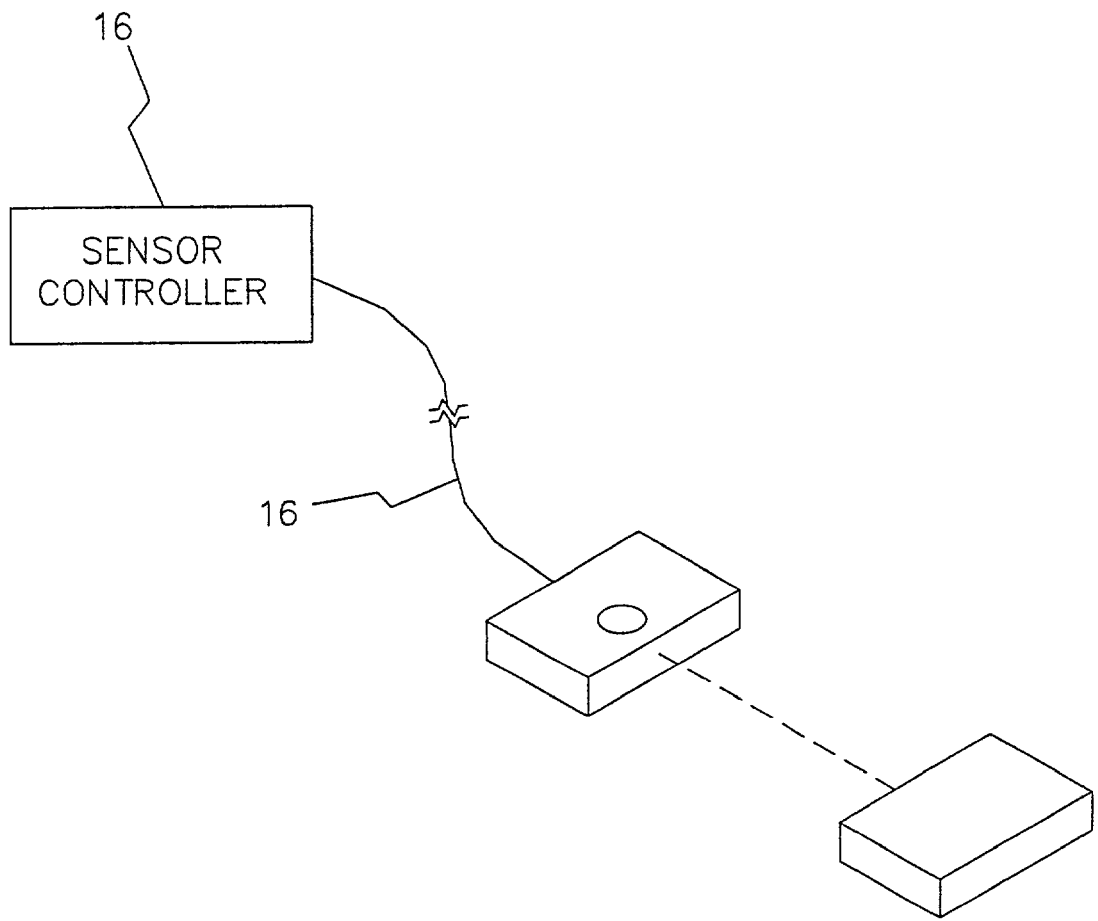
FIG. 1 shows a plurality of sensors implanted within body tissue and/or fluids connected to a sensor controller.

Appendix A illustrates various glucose calibration algorithms that may be used as part of the present invention.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Turning first to FIG. 1, there is shown a schematic diagram of a plurality of implantable sensors 10a, . . . 10n, implanted within body fluids or tissue 12 or other desired area. The sensors 10 may comprise any type of implantable sensor, e.g., a temperature sensor, an oxygen sensor, a $CO_2$ sensor, a glucose sensor, a pH sensor, a salinity sensor, or the like. Each sensor 10 typically includes at least one electrode 14 adapted to interact with or sense some prescribed substance that may be present within (or absent from) the tissue 12 to varying degrees. To this end, each sensor 10 operates independently of the other sensors being used, yet each is implanted within the same general area of the tissue or fluids 12.

It is noted that some types of sensors, e.g, a temperature sensor or an activity (motion) sensor, need not necessarily have an electrode 14 that is exposed to the tissue or fluids 12 in order to perform their sensing function. For purposes of the broad aspects of the present invention, it will thus be appreciated that what is important is not whether the sensor has one or more electrodes, but rather that the sensor be capable of accurately sensing a parameter of interest, and that the integrity of such sensing be regularly checked or verified.

The sensors 10 are connected to a sensor controller 16 by way of a suitable coupling cable 18. The controller 16 may or may not be implantable. If the controller 16 is not implanted, then appropriate means are employed, as is known in the art, along the length of the cable 18 to transcutaneously interface with implanted sensors 10 so that appropriate signal communication may take place between the implanted sensors 10 and the controller 16. A common transcutaneous interface technique known in the art is inductive coupling, using both implanted and external coils. Alternatively, optical, magnetic, or other types of signal transmission could be used to achieve a transcutaneous signal link through the cable 18.

In accordance with the present invention, integrity tests are performed at specified intervals, e.g., periodically, at least once every 1-24 hours, or at other specified intervals, such as whenever a measured parameter is out of tolerance, that check the performance and basic operation of the sensors 10. This is done to safeguard the patient from a malfunctioning sensor, which (depending upon the function of the sensor) could prove very dangerous to the patient. Alternatively, where the sensors are implanted or positioned in a remote, inaccessible area, e.g., deep in the ocean or within a sealed saline solution over a long period of time, such integrity tests, performed at specified intervals, provide confidence in the data produced by the sensors.

The integrity tests may be initiated from the controller 16, or may be initiated from circuitry that forms an integral part of the sensor 10. When the integrity tests are performed, the results of such tests are transmitted to the controller 16, where the controller analyzes such results and/or makes the results available (e.g., through an appropriate telecommunicative link, such as an inductive, magnetic, rf, or optical link) to an external or other device (such as an external programmer) adapted to display or communicate the test results to the patient, medical personnel, or others who are monitoring the test data. The use of external programmers to interface with implantable devices is well known in the art, as evident from, e.g., U.S. Pat. No. 5,609,606, incorporated herein by reference.

Various types and kinds of integrity tests may be performed in connection with the sensors 10 in accordance with the present invention. One basic integrity test that may be made involves monitoring the sensor output signal, i.e., that signal which provides a measure of whatever it is that the sensor is measuring, from each of a plurality of sensors located within the same general tissue area, to see if there is a consensus between such measurements. That is, assume there are five identical sensors all implanted within the same general tissue area, and all configured to measure the same substance within that tissue area. If all five sensors provide approximately the same measurement data, e.g., within about 20% of each other, then that indicates—i.e., provides integrity test data—that all five sensors are performing properly. Should four of the sensors agree, and one disagree, then that indicates the disagreeing sensor is likely malfunctioning. As a result of such finding, all sensor data subsequently obtained from such malfunctioning sensor may be ignored, or alternatively the sensor may be disabled.

In a similar manner, if three sensors are used, a periodic or other scheduled or triggered check of the output signal from all three sensors may reveal agreement (consensus) or lack thereof. If there is agreement, then all sensors are presumed to be operating correctly. If two sensors agree, but one does not, then the one that does not agree is likely not functioning properly. If all three sensors disagree, then that could trigger a need for recalibration, or other appropriate step, to determine which sensor is functioning properly.

Other types of integrity tests that may be performed, depending upon the capabilities of the sensors 10, include impedance (e.g., resistance) and/or voltage measurements, e.g., measuring the impedance and/or voltage from the electrode 14 of one sensor 10a, to a reference electrode, e.g., at the controller 16 (if implanted), or at some other location. Alternatively, the impedance and/or voltage may be measured between the electrode 14 of one sensor 10a and another sensor 10n.

As indicated, a preferred sensor 10 with which the present invention may be used, is a glucose sensor 52 of the type that is described in the above-referenced '772 U.S. patent, or the above-reference patent applications. This preferred glucose sensor 52 is electrically depicted in FIG. 2A. Such sensor 52 is based on the "enzyme electrode" principle wherein an enzyme reaction and an electrochemical detector are utilized to measure the concentration of glucose. More particularly, the sensor includes at least three electrodes: a first working electrode W1, a collector electrode C, and a reference electrode R, submersed in a suitable conductive liquid 54, such as a saline solution of water ($H_2O$), confined by a first membrane 55. A fixed trim voltage V is applied between the electrode R and the electrodes W1 and C. A suitable enzyme E is immobilized in a second membrane 56 so as to surround the first working electrode W1. For a glucose sensor, the enzyme E is preferably glucose oxidase (GO).

During operation, when the sensor is implanted in the patient's tissue, e.g., blood, the enzyme E is exposed to the glucose and oxygen present in the tissue. Both the glucose and oxygen diffuse from the tissue into the membranes 55 and 56 whereat, in the presence of the enzyme E, they react to produce gluconic acid and $H_2O_2$. The rate of the reaction is directly related to the concentration of glucose in the tissue and is monitored by an electrochemical oxygen detector made up of the electrodes W1, R and C, a current source 58 and a voltage source 60 (FIG. 2A). The working electrode W1 and the counter electrode C are preferably made or coated from platinum (Pt). The reference electrode R is typically made form or coated with silver chloride. When a trim voltage V is placed across the electrodes R and W1, as well as across R and C, a current I tends to flow between the electrodes C and W1. (Assuming the voltage source is an ideal voltage source, with infinite impedance, no current flows through the reference electrode R.) When the above chemical reaction occurs, oxygen is consumed at the working electrode W1. The amount of oxygen remaining can be determined as a function of the amount of current flowing through the working electrode W1. More particularly, it can be shown that the relationship between the current (I) that flows and the trim voltage (V) varies as a function of the oxygen concentration as shown qualitatively in FIG. 2B. For a high concentration of oxygen ($O_2$), a curve 62 establishes the relationship between I and V. For a low concentration of $O_2$, a lower curve 64 establishes the relationship between I and V. For each value of $O_2$ concentration between the high concentration curve 62 and the low concentration curve 64, another curve (intermediate the curves 62 and 64) establishes the current-voltage relationship, with each curve of the family corresponding to a different $O_2$ concentration.

To measure the $O_2$ concentration using a circuit such as is shown in FIG. 2A, all that need be done is to force the trim voltage V to be affixed value $V_R$, where $V_R$ typically ranges between 0.3 and 0.7 volts, e.g., 0.5 volts. This is done by adjusting the current I until the desired trim voltage $V_R$ is obtained. At the voltage $V_R$, the relationship between the current I and the oxygen $O_2$ is substantially linear, as depicted qualitatively in FIG. 2C. Thus, using a sensor such as is functionally depicted in FIG. 2A, the amount of oxygen remaining at the working electrode W1 is simply a function of the current I required to force the trim voltage V to $V_R$.

Since the oxygen detector is monitoring the oxygen not consumed by the enzyme reaction, the detector signal, i.e., the current I, is inversely related to the glucose concentration. The more glucose in the tissue, e.g., the blood, the less oxygen will be detected by the oxygen detector with the enzyme present.

Figure 3:
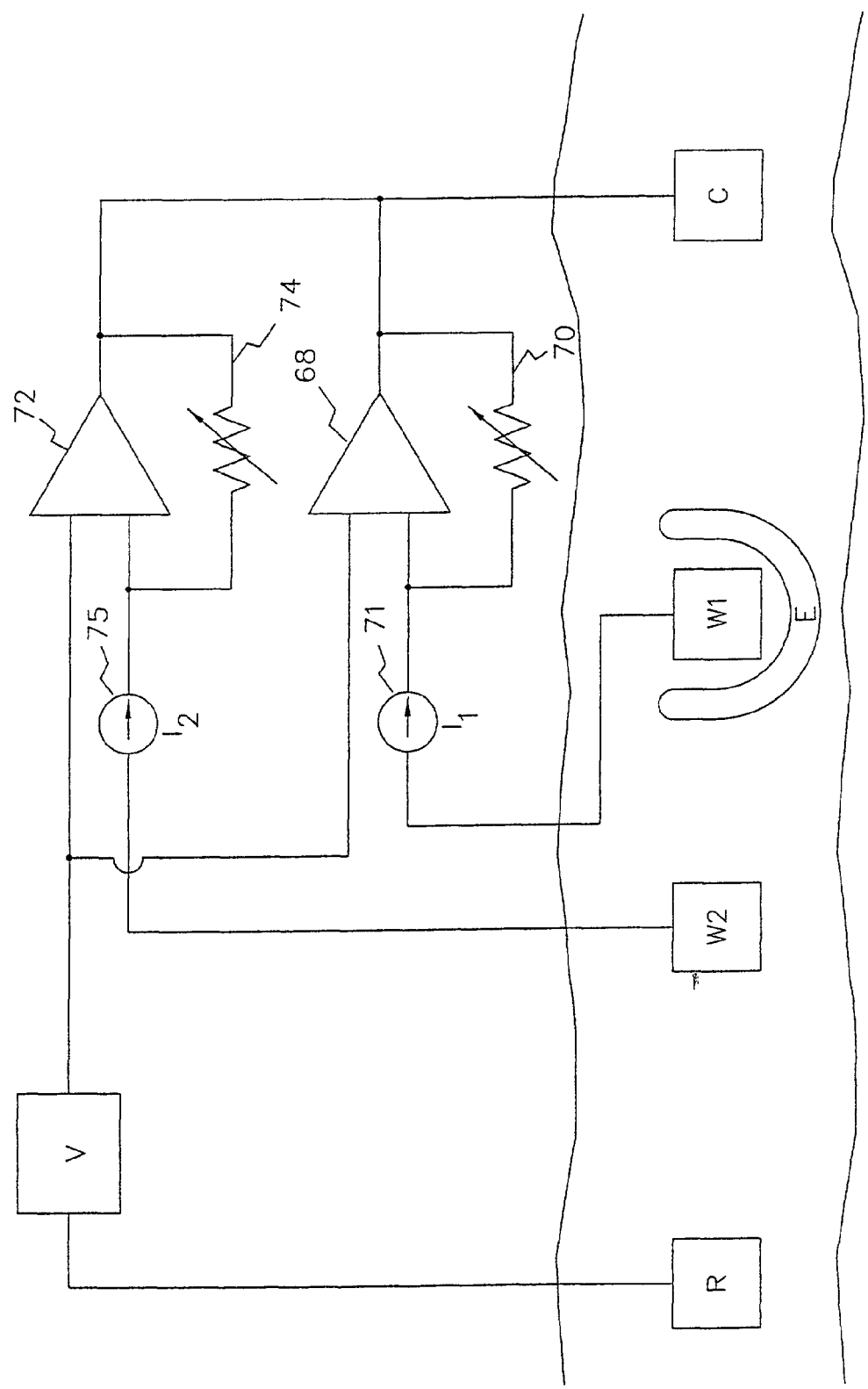
FIG. 3 shows an electrical schematic diagram that depicts the use of two working electrodes within a glucose sensor, one to provide a measure of the oxygen that reacts with the glucose in the blood (and thereby provides a measure of the glucose in the blood), and another to provide a reference baseline measurement of the background blood oxygen concentration (which measurement is used for compensation)

To improve the accuracy of the oxygen determination made by the detector of FIG. 2A, and in particular to allow compensation for changes in the background blood or tissue oxygen concentration, a second working electrode W2 is employed at a location in the sensor that is not surrounded by the enzyme E, as shown in FIG. 3. As such, the electrode W2 simply detects background oxygen concentration (not oxygen consumed by the enzyme reaction), and thus provides a means of compensating the oxygen measurement made using the first working electrode W1 for background oxygen.

As seen in FIG. 3, a first adjustable current source is realized from an operational amplifier 68 and a feedback loop 70. A second adjustable current source is likewise realized form an operational amplifier 72 and a feedback loop 74. Both the first and second current sources apply their respective currents to the collector electrode C. A measurement of the current I1 flowing through the first working electrode W1 is provided by current sensing element 71. Similarly, a measurement of the current I2 flowing through the second working electrode W2 is provided by current sensing element 75.

In operation, the trim voltage V is set to the desired fixed trim value $V_R$, and the currents I1 and I2 are measured. The current I1 provides a measure of the oxygen remaining at the working electrode W1, which in turn provides an inverse measure of the glucose concentration in the blood or other tissue. The current I2 provides a measure of the background oxygen in the blood or tissue, and thus provides a means for compensating the I1 measurement for background oxygen variations. The absolute quantitative value of the glucose level is determined by comparison of the two detector signals, i.e., the two currents, I1 and I2, and by reference to a previously determined calibration. The basic calibration technique is described below in conjunction with the flow chart of FIG. 7 and the calibration curves of FIGS. 8A, 8B and 8C. More detailed information relative to the various calibration algorithms that may be used are described in Appendix A. Appropriate processing to obtain such quantitative measure of the glucose concentration is performed by appropriate processing circuits, typically included within the controller 16 or an external programmer.

Turning next to FIGS. 4A, 4B, 4C and 4D, additional details are provided concerning the preferred manner of making a sensor 10 in accordance with the invention. Further details may be found in the patent applications referenced above. Basically, the sensor includes a substrate 100 on which an integrated circuit (IC) chip 102 is mounted and connected to selected other electrical components, such as a capacitor 104, via conductive traces that are deposited or etched on the surface of the chip 100. A suitable cover 106 fits over the electrical components 102, 104, and connective traces, and is hermetically sealed to the substrate 100 so as to form an hermetically sealed portion of the sensor 10. Electrical contact with the circuits and components within the hermetically sealed portion is made via pads 108 and 110 and 109 and 111 located on respective ends of the substrate 100. These pads have conductive traces connected thereto that tunnel into the hermetically sealed portion through the ceramic substrate, in the manner taught in U.S. patent application Ser. No. 08/515,559, filed Aug. 16, 1995, incorporated herein by reference. Essentially, these traces pass vertically down into the substrate 100, then horizontally across the substrate to a point underneath the hermetically sealed portion, and then vertically back up into the hermetically sealed portion.

Figure 4:
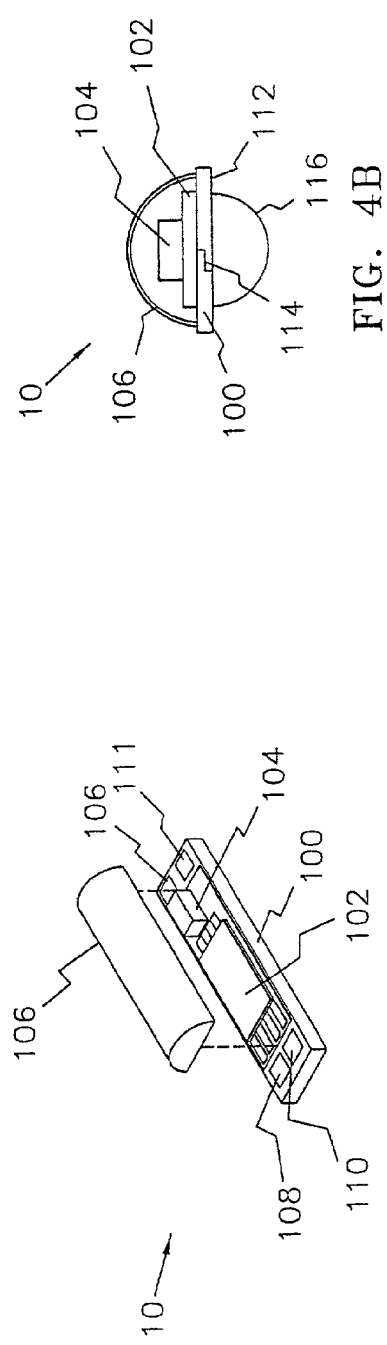
FIG. 4A depicts a partial exploded view of a glucose sensor of a type with which the present invention may be used.
FIG. 4B depicts a sectional end view of the sensor of FIG. 4A.
FIG. 4C shows a bottom view of the sensor of FIG. 4A.
FIG. 4D is a block diagram that illustrates the manner in which several, e.g., three, glucose sensors may be daisy chained together and connected to a controller.

In a similar manner, conductive traces pass through the substrate 100 from the IC chip side of the substrate to an electrode side 112 of the substrate, which (as drawn in FIG. 4B) is the underneath or bottom side of the substrate 100. Each of the traces that pass through the substrate from the IC side to the electrode side do so in a stair-step manner, as illustrated in FIG. 4B by the trace 114, so as to preserve the seal of the hermetic portion. That is, there are no traces that tunnel through the substrate which do so in a single vertical or straight segment. Rather, there is always at least one a vertical segment connected to at least one horizontal segment, as taught in the above-referenced patent application (Ser. No. 08/515,559). In this manner, the stair-step tunneling traces 114 function as electrical feedthroughs into the hermetically sealed portion of the sensor.

On the electrode side 112 of the substrate 100, a plurality of electrodes are arranged in a suitable pattern, as illustrated in FIG. 4C. These electrodes may include, e.g., a first working electrode W1, a second working electrode W2, a counter electrode CNTR, a first reference electrode REF1, a second reference electrode REF2, and a platinum black electrode Pt, and may be arranged in various patterns. As taught in the '772 patent and the above-reference patent applications, these electrodes are all electrically insulated from each other by placing a layer of insulation, such as alumina, between the electrodes. A thin inner sheath of silicone rubber then covers the substrate electrodes, and includes a thin pocket or space above the electrodes wherein a suitable conductive fluid, such as PHEMA, is maintained. This thin inner sheath is covered by a much thicker sheath 116, also made of silicone rubber or an equivalent material. A pocket, or window, is formed within this sheath 116 above the working electrode W1, wherein the GOX is placed.

For purposes of the present invention, the important feature of the sensor 10 is that each of the plurality of electrodes on the electrode side (which comprises the non-hermetic portion of the sensor) of the substrate 100 are electrically connected with the hermetically-sealed circuitry on the IC side of the substrate 100.

A preferred arrangement of the sensors 10 is to connect a plurality of such sensors in a daisy chain, as depicted in FIG. 4D. In FIG. 4D, three sensors 10a, 10b, and 10c are thus connected in series, although this is only exemplary. Any number of sensors could be connected in this manner. Advantageously, the pads 108, 110, 109, 111 associated with each sensor, facilitate such daisy chain connection. Moreover, as described in the above referenced patent application Ser. No. 08/928,867 (Now U.S. Pat. No. 5,999,848), such connection may be effectuated using just two conductors 118 and 120, yet control commands and data may still be readily transferred between the sensors 10a, 10b and 10c and/or a controller 16. It is noted that the two conductors 118 and 120 are insulated conductors, and that at the point where they bond with the pads 108 and 110, or 109 and 111, they are covered with epoxy, or other suitable insulator, but such covering does not create an hermetic seal. That is, there will be some leakage to the pads 108-111. However, as explained in the above reference patent application, that is one of the advantages of the present sensor—its ability to function even in a leaky or noisy environment.

Figure 5:
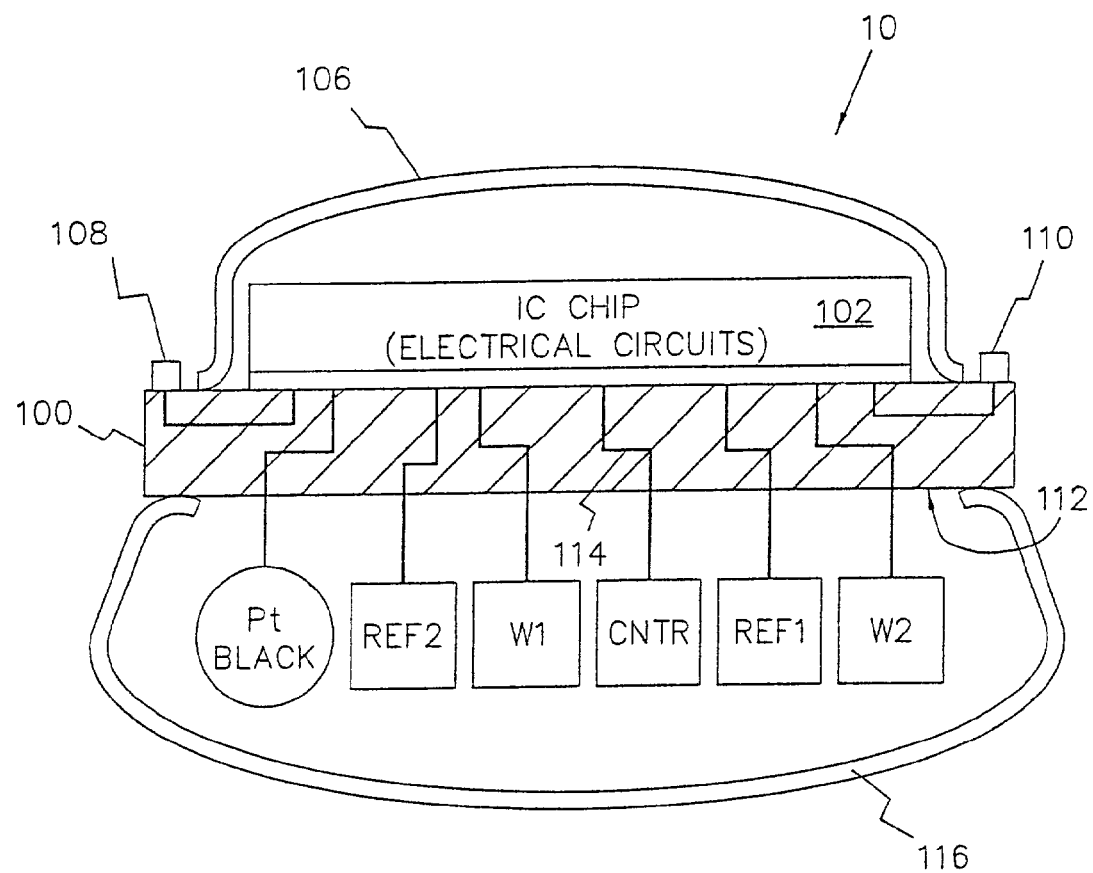
FIG. 5 conceptually illustrates the various components of the glucose sensor and their interrelationship relative to integrity tests that may be performed by the present invention.

Turning next to FIG. 5, there is shown a schematic representation of the preferred sensor 10, including the various electrodes located on the non-hermeitcally sealed portion on the electrode side 112 of the substrate 100, and the IC chip 102 located on the hermetically sealed portion of the substrate 100 (the other side of the substrate 100), and the stair-step feedthrough connections 114 that electrically connect the two portions to each other. The IC chip 102 may include various types of circuits for processing and handling measured signals obtained via the electrodes or otherwise generated or sensed within the sensor 10, and/or for decoding and responding to various commands received through the connections 108, 110 from a controller 16. The types of circuits that are used in connection with a preferred glucose sensor are fully described in the previously referenced patent applications. These circuits include, e.g., a line interface circuit, a low power rectifier circuit, a current-to-frequency converter circuit, multiplexer circuits, decoder/encoder circuits, and the like.

Figure 6:
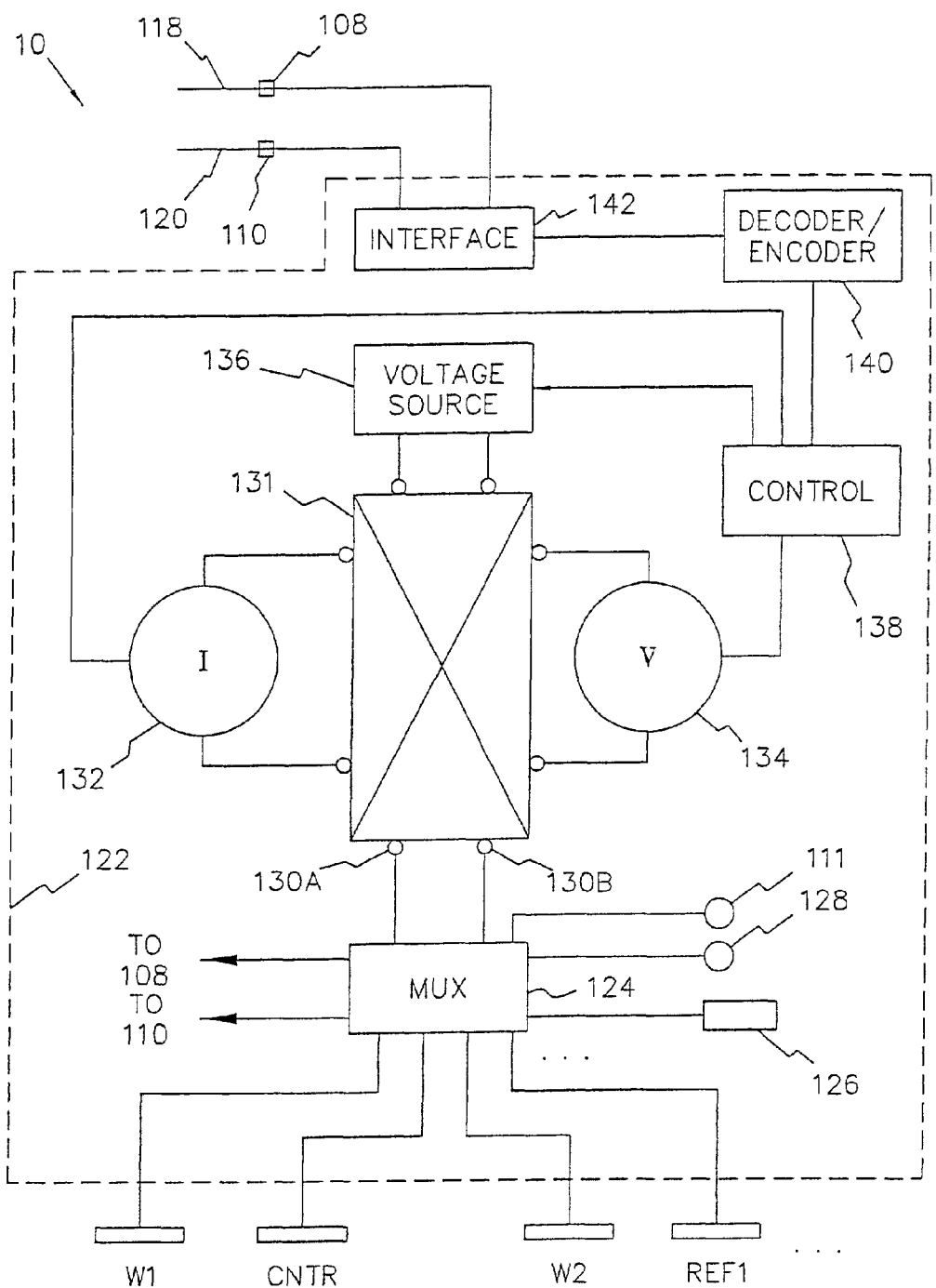
FIG. 6 is a block diagram of the circuits included within the sensor that are used to perform the integrity tests of the invention.

For purposes of the present invention, however, the types of circuits that need be included within the IC chip 102, or otherwise available within the sensor 10, are shown in the block diagram of FIG. 6. It is recognized that these circuits, as shown in FIG. 6, may not represent all the circuits that may be included within the sensor 10. This is because the types of circuits used with the sensor 10 will be a function of what kind of sensor the sensor 10 is. For purposes of the present invention, however, it does not matter what type of sensor the sensor 10 is. All that matters is that the sensor include some means of checking its own performance, e.g., some means for performing one or more integrity tests, and then communicating the results of such test to a user or otherwise using the results to confirm proper operation of the sensor. Hence, all that is shown in FIG. 6 are those kinds of circuits that would most likely be needed in order to practice the integrity tests of the present invention. It is noted that in the preferred implantable glucose sensor, as described, e.g., in the above-reference patents and patent applications, that circuits are included on-board the sensor chip, in one form or another, which allow the measurement functions described in connection with FIG. 6 to be carried out.

In FIG. 6, the dotted line 122 represents the boundaries of the hermetically sealed portion of the sensor. Not included within the hermetically sealed portion 122 are a plurality of electrodes W1, CNTR, W2 and REF1, and connection pads 108, 110, connected to conductive leads 118 and 120. The number and types of electrodes is exemplary. For purposes of the present invention, there will typically be at least one electrode not included within the hermetically-sealed portion 122, and there could be more electrodes than is shown in FIG. 6.

The circuits included within the hermetically sealed portion 122 include a multiplexer (MUX) 124 that selectively connects any two of the electrodes external to the hermetically-sealed portion or any additional sensing element 126 or reference points 110, 128 within the hermetically-sealed portion to two measurement points 130A and 130B. A current measurement device 132 (e.g., a current meter), a voltage measurement device 134 (e.g., a voltage meter), and a variable voltage source 136 may then be selectively connected to the measurement points 130A and 130B through a connection matrix 131. That is, with the connection matrix 131, the voltage between any two reference points, e.g., between any two electrodes selected by the MUX 124, and/or the current flowing between any two reference points selected by the MUX 124, while a specified potential is applied between the selected reference points, may be measured.

The measurement circuits shown in FIG. 6 are controlled by a control circuit 138. The control circuit, in turn, receives commands from, or sends data to, a decoder/encoder circuit 140. The decoder/encoder 140 is coupled to the input lines 118 and 120 (which are connected to a suitable controller 16—see FIG. 1 or FIG. 4D) through an interface circuit 142. All of these circuits may be as described in the previously-referenced patent applications, or may be of any other suitable design. None of these circuits, per se, comprise the present invention. Rather, they are simply exemplary tools that may be used to help carry out the invention.

The on-board control circuit 138 may be, for example, a microprocessor circuit, including memory circuits for storing an operating program that controls which integrity tests are performed and in what sequence. Alternatively, the control circuit 138 may be a simple state machine, controlled by command signals received from the external controller 16, in which case control of the integrity tests can be made from the external controller 16.

With reference now to both FIGS. 5 and 6, the integrity tests that may be performed as part of the present invention will be described. In general, such tests include measuring the voltage and/or current that flows between any two points, which two points may comprise two external points (not within the hermetically sealed portion 122), or an external point and an internal point, such as the reference point 128 (which may comprise, e.g, a ground or common reference point). With such voltage and/or current measurements, the impedance (resistance) between the selected two points, e.g., electrodes, can be determined. The impedance measurements, in turn, provide valuable information regarding whether the sensor 10 is functioning properly. Moreover, by changing the voltage potential that is applied between the two points being monitored, various operating points of the circuitry within the sensor IC chip 102 may be obtained and analyzed, thereby confirming, e.g., that the circuits are operating in accordance with a desired design. For example, for the preferred glucose sensor, the basic operating curves shown in FIG. 2B may be confirmed, thereby confirming the accuracy of the measurement relationship shown in FIG. 2C.

In addition to current, voltage, and impedance measurements, other important measurements can also be made. For example, the internal sensor 126 may comprise, in one embodiment, a temperature sensor that provides an electrical signal indicative of the temperature on the sensor chip. Simply conveying the temperature measurement could serve as an integrity test because if the temperature is out of an anticipated range, then that could provide an indication that something is not working correctly within the sensor. In another embodiment, the internal sensor 126 may comprise an motion or activity sensor, so that if a signal was received that did not agree with a known and anticipated pattern of motion or activity, that too could serve as a valuable indicator of whether the sensor is performing as designed. Still further, the reference point 128, or another internal reference point, could be coupled to the internal voltage source 136 so that the voltage potential of such source could be measured. Again, being able to periodically or regularly measure the voltage potential available within the sensor could provide valuable information regarding whether the sensor is performing as designed. Additionally, the reference point 128 may be connected to the case of the sensor, or the case of the sensor may itself comprise a reference electrode.

When the sensor 10 comprises the preferred glucose sensor, the desirable sensor parameters to monitor may include:
(1) verifying the platinum electrode current stability for oxygen monitoring, and for current sinking;
(2) checking the silver chloride to gel voltage stability;
(3) checking the integrity of the gel pH;
(4) checking the electrical conductivity of the saline solution;
(5) verifying the integrity of the aluminum oxide and/or other, e.g., epoxy, insulation;
(6) determining the GOX activity level; and
(7) checking the accuracy of the oxygen sensor.

Advantageously, these sensor parameters can be monitored, on a regular basis, e.g., one every 1-24 hours (or in accordance with another desired schedule) as controlled by an on-board microprocessor or equivalent control circuit (or by a microprocessor or equivalent within the remote controller 16) by performing the integrity tests described below.

First, the leakage current can be measured between e.g., between the outside body solution and an uninsulated platinum black electrode or other reference point that is exposed to the body solution. With reference to FIG. 5, for example, such measurement could be made by measuring the resistance between the case cover 106 (connected through point 128 to the MUX 124, FIG. 6) and each of the pads 108 and 110. Alternatively, an additional uninsulated Pt.-Black electrode could be included on the substrate 100. When performing such measurement, any signals being transmitted over the coupling wires 118 and 120 would be stopped for a prescribed time period T1, e.g., 100 msec, and the leakage current between the pads 108 or 110 and the case 106, or between pads 108 and 110 (or between pads 109 and 111, FIG. 4A) could be measured. This leakage current should be within a certain range, as a function of the conductivity of the saline solution within which the sensor is immersed and other factors. A typical value of leakage current might be 100 µA.

Next, the leakage between any of the electrodes, e.g., the electrodes W1, W2, CNTR, REF1, REF2 and the conductors (pads 108, 110) may be measured. This measurement could also be measured between any of the electrodes and the case, if the case is connected or connectable to the measurement circuitry. This leakage current should be very small, i.e., it should not exceed $I_0$, where $I_0$ is on the order of 1 pA. If the leakage current does exceed $I_0$, i.e., if the measured leakage current is between about 1 pA-1000 pA, then that indicates the sensor's performance is borderline, and there could be a problem for statistical purposes. If the measured leakage current is within the range of, e.g., 10 nA-1 µA, then that means the sensor will provide erroneous values.

Next, a resistance measurement may be made between any two electrodes. For example, the resistance between the W1 and W2 electrodes effectively measures the resistance of the PHEMA (or conductive solution that is confined to the region of these electrodes). This resistance should be less than about 1000 ohms. If the resistance is in the range of 10K-100K ohms, then that means the sensor readings would not be accurate.

As a further integrity test, the flatness of the current-voltage curve (see FIG. 2B) may be checked. This is done, e.g., by measuring the current that flows between the W1 and W2 electrodes for at least two different reference voltages. Preferably, three points are taken, a center reference voltage, corresponding to $V_R$ in FIG. 2B, of, e.g., 0.5 volts is applied and the current flow is measured. Then, the reference voltage is varied ±0.1 volts, and additional currents are measured at each point. From these measurements, the slope of the I-V curve can be checked. It should be relatively flat, as qualitatively shown in FIG. 2B. If the slope is <2%, then that is good. If the slope is linear to zero, that is bad. That is, once the plateau shown in FIG. 2B ceases to exist, the sensor is not able to perform its oxygen-sensing function. As another criteria, the slope of the I-V curve in its flat region may be measured when the sensor is first manufactured. This initial slope value can then be saved as a reference value. If a subsequent measurement of the slope is more than 20% different than the reference value, then that indicates the sensor is bad.

Another integrity test is to check the integrity of the insulation layer that is used to separate the electrodes. As explained above, this insulation layer is placed between the electrodes, but does not cover these electrodes. The test may be performed by placing a separate electrode, e.g., REF2, on the electrode surface 112 and completely coating this electrode with the insulation material, e.g., alumina $Al_2O_3$. Then, the impedance between this covered electrode and any other electrode or reference point can be measured. If the insulation layer is intact, then this impedance should be very high, near infinite impedance.

An additional integrity test is to measure the CNTR to REF1 potential. For a given $O_2$ concentration level, the CNTR-REF1 voltage should be stable. No drift should be present. Thus, this measurement should be taken several times in succession over a relatively short time period (to assure the $O_2$ level does not significantly change) and these successive measurement values should then be compared to each other. Any change more than about ±20% would indicate that there is a problem with the sensor.

An important integrity test, as has previously been mentioned, is to compare the measured $O_2$ values from a plurality of sensors, e.g., three sensors, that are implanted within the same general tissue area. These measurements should all agree with each other within an acceptable tolerance, e.g., ±10%. If there is disagreement, then appropriate decision steps are taken to identify the erroneous sensor, e.g., majority rules. If all sensors disagree, then recalibration is called for. As a related integrity test, the calculated glucose concentration for each of the plurality of sensors can also be compared.

Yet another integrity test that can be performed is to measure the open circuit voltage between specified electrodes. For example, an open circuit voltage can be measured between a separate platinum black electrode and the reference electrode. With respect to FIG. 5, this means measuring the open circuit voltage between the Pt.-Black electrode and the REF1 electrode. This voltage should be zero. Similarly, the open circuit voltage between the electrodes W2 and CNTR can be measured. It, too, should be zero for 0 current flow. Likewise, the open circuit voltage between W1-CNTR should be zero for 0 current flow. A set voltage, e.g., $V_R$, should exist between W2-REF1 and W1-REF1.

In general, then, the integrity tests for the preferred glucose sensor include current leakage tests, resistance tests, voltage tests, and I-V characteristic tests (curve flatness). Experience indicates that the results of these integrity tests, e.g., the amount of leakage current that occurs, will start to increase or significantly change from prior values before major sensor problems occur. It is therefore important to perform these integrity tests on a regular basis, e.g., once every day, while the sensor is within the patient. A good time to perform the tests is at night when the patient is sleeping and when the $O_2$ concentration is stable.

Data communication between the implanted sensor and the controller 16 may occur using any suitable type of modulation scheme and/or carrier transmission system, as is known in the art. One type of data transmission scheme is as disclosed in applicants patent application Ser. No. 08/928,867 (Now U.S. Pat. No. 5,999,848), previously incorporated herein by reference.

The results of the sensor tests, if problematic, may be communicated through the controller 16 (see FIG. 1) to appropriate medical personnel. Preferably, an appropriate message is communicated to the patient, as soon as the external programmer is coupled to the system, or through other appropriate signaling or communication means, to inform the patient that he/she should contact his/her doctor or clinic as soon as is reasonably possible. The patient need not be told the exact nature of the problem identified by the integrity tests, only that he/she should contact his medical doctor or clinic for evaluation. The doctor or other medical personnel could then evaluate the data and make a determination if a true problem exists, and if so, what type of corrective actions if any, is needed.

One type of corrective action that may be needed, either on an automatically-scheduled basis or as the need arises, is a calibration or recalibration of the sensor(s). Appropriate algorithms for calibrating or recalibration the preferred glucose sensors are shown in Appendix A, incorporated herein by reference.

Closely related to calibration of the sensor(s), where the sensor(s) comprise a glucose sensor of the type disclosed in the referenced patent applications, is the manner in which the glucose concentration is determined using the sensor(s). The basic approach for determining glucose concentration is illustrated in the flow diagram of FIG. 7. As previously described, the glucose sensor determines the amount of glucose present in the tissue being monitored by measuring the amount of oxygen in the presence of a prescribed enzyme. The sensor provides, as an output signal, an electrical current. In the preferred embodiment, two electrical currents are provided as the output signal of the sensor. A first electrical current flows through the first working electrode W1 (the one which is surrounded by GOX, or other suitable enzyme) and provides a measure of the oxygen at the first working electrode (which oxygen amount is inversely related to the glucose that is present). A second electrical current flows through the second working electrode W2 and provides a measure of the background oxygen present at the second electrode W2.

Figure 7:
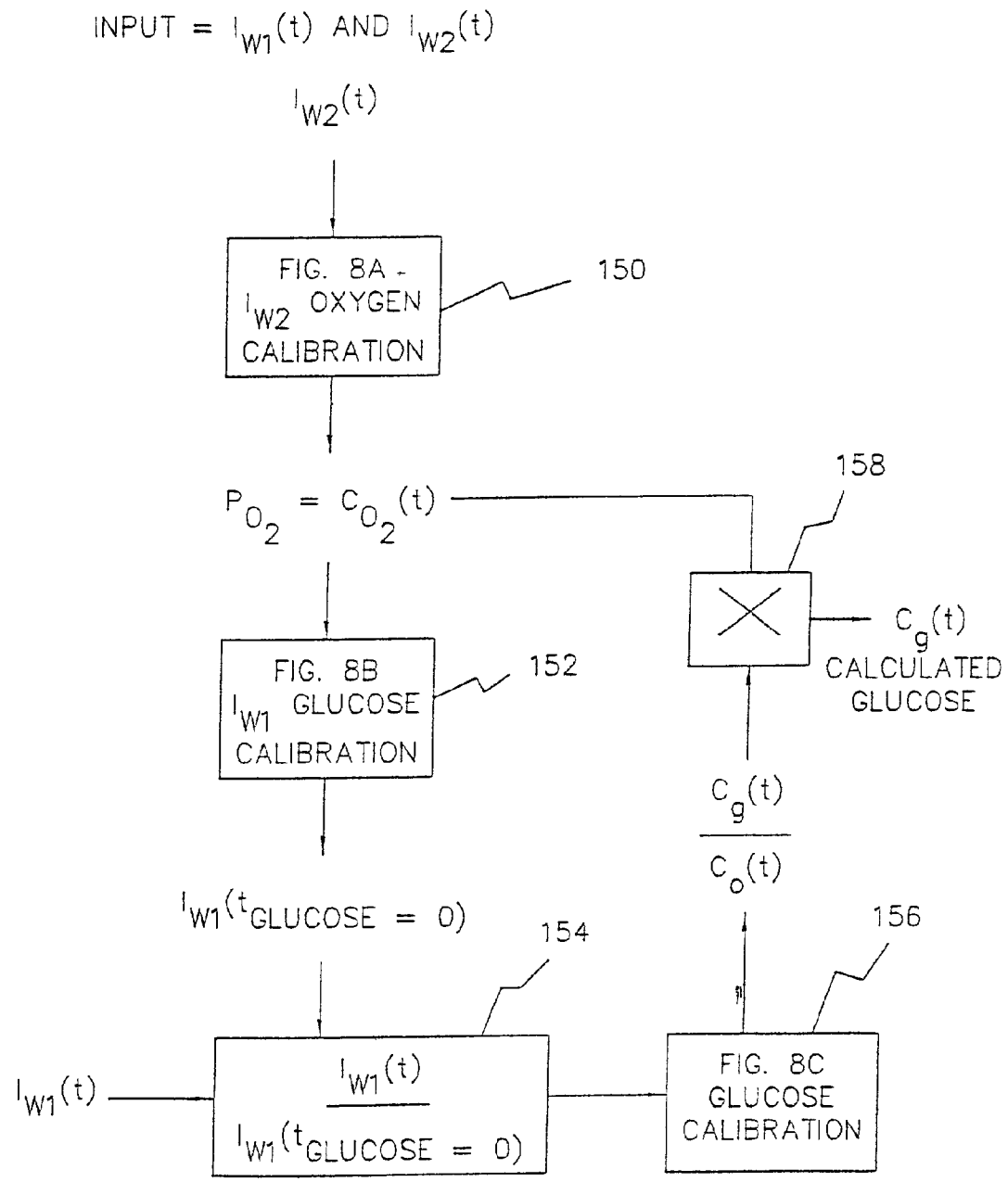
FIG. 7 is a flow diagram that depicts one manner in which the preferred sensor makes a glucose measurement.

With reference to FIG. 7, it is seen the two currents used to measure the glucose level may be designated as $I_{W1}(t)$ and $I_{W2}(t)$. In FIG. 7, there currents are identified as "Input" currents (even though they are also output currents from the sensor), because they serve as the starting point, or "input", in order to derive the glucose concentration.

Figure 8A:
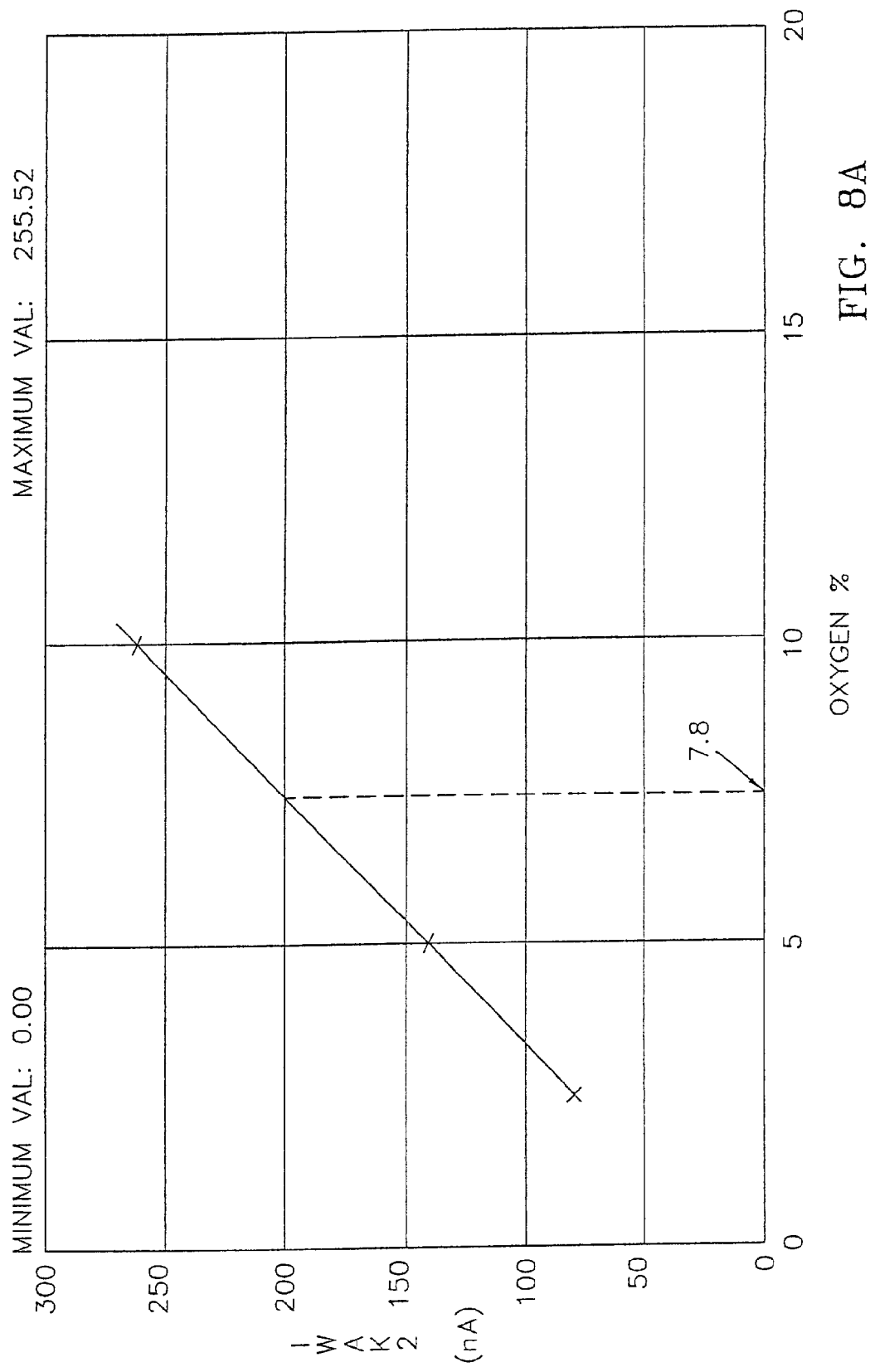
FIGS. 8A, 8B and 8C are representative calibration curves that are used in carrying out the measurement method illustrated in FIG. 7.

As shown in FIG. 7, the second current, $I_{W2}(t)$, is measured and the value is applied (see block 150 of FIG. 7) to an appropriate conversion or transfer curve, e.g., of the type illustrated in FIG. 2C or an equivalent (e.g., a look-up table would serve the same function) in order to convert the measured current to a measure of oxygen. An example conversion curve used for this purpose is shown in FIG. 8A. For example, with reference to FIG. 8A, if the current $I_{W2}(t)$ is 200 nA, then that translates to a background oxygen concentration, $PO_2$, of about 7.8%. This percent oxygen can then be converted, as required, to a measure of the background oxygen concentration. $CO_2(t)$, by knowing the volume and pressure associated with the sample size. The units of the background oxygen concentration $CO_2(t)$ are typically expressed in mg/dl at a specified pressure (mmHg).

Figure 8B:
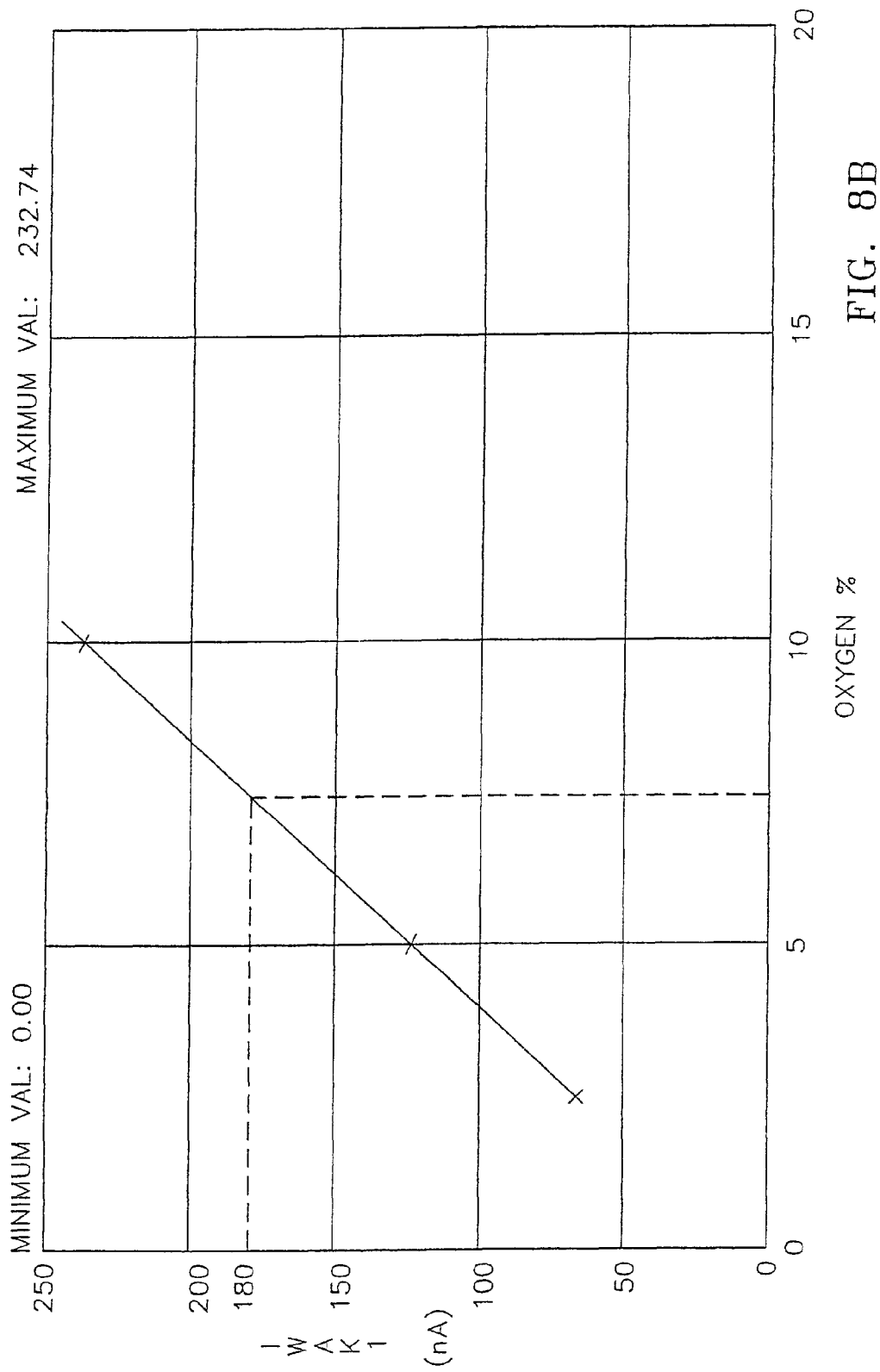

Once the background oxygen concentration $PO_2$ is determined, this value may be used to compensate for the measurement taken at the enzyme-surrounded electrode W1 see block 152 of FIG. 7). To achieve this compensation, the value of $PO_2$ from FIG. 8A is taken to a second transfer curve, e.g., as shown in FIG. 8B, to determine a corresponding first current value, $I_{W1}(t_{GLUCOSE}=0)$. For example, if $PO_2$ is 7.8%, then from FIG. 8B it is seen that $I_{W1}(t_{GLUCOSE}=0)$ is about 180 nA.

Figure 8C:
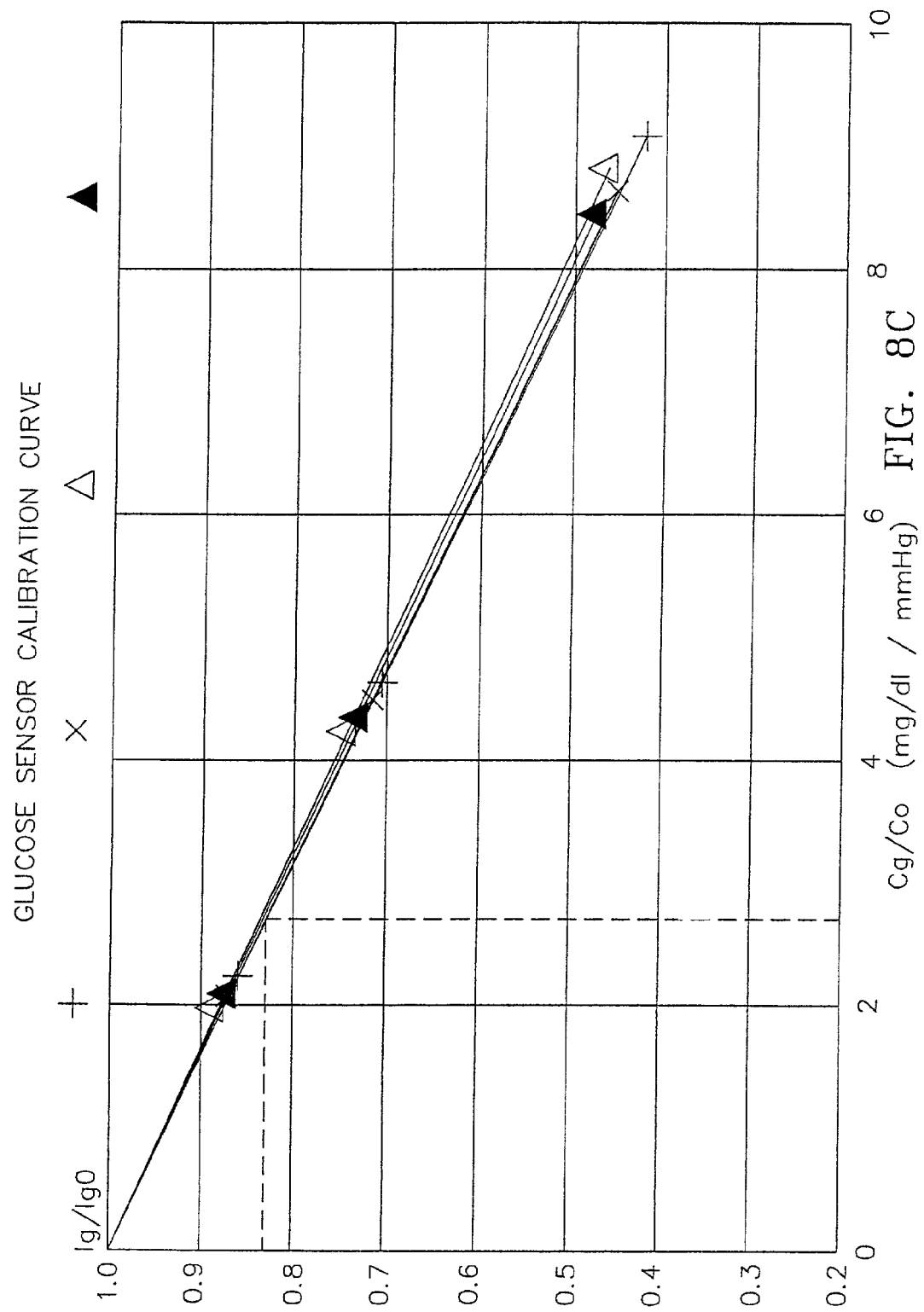

A ratio of the two current values, the determined $I_{W1}(t_{GLUCOSE}=0)$ and the measured $I_{W1}(t)$, is next determined (block 154 of FIG. 7). By way of example, if $I_{W1}(t)$ is measured to be 150 nA ($I_{W1}(t)$ should always be less than $I_{W1}(t_{GLUCOSE}=0)$) then the ratio of $I_{W1}(t)$ to $I_{W1}(t_{GLUCOSE}=0)$ would be 150/180=0.833. This ratio is then applied (see block 156 of FIG. 7), to a glucose sensor calibration curve, as shown in FIG. 8C. From such glucose calibration curve it is seen that the ratio of glucose concentration to oxygen concentration, $C_g(t)/C_o(t)$, is about 2.7 mg/dl/mmHg. The previously-determined background oxygen concentration, $CO_2(t)$, is then multiplied by this ratio (block 158) in order to calculate the measured glucose concentration, $C_g(t)$.

As described above, it is thus seen that the present invention provides, within an implantable sensor, a means for automatically verifying the integrity of the sensor on a periodic basis. This is done, in one embodiment, through the use of electrical/electronic circuits included as part of the sensor circuitry which automatically carry out one or more integrity tests on the sensor on a scheduled basis, and which then eventually report any out-of-tolerance conditions and/or other problematic or informational data to appropriate personnel so that needed corrective action, if any, may be taken.

While the invention herein disclosed has been described by means of specific embodiments and applications thereof, numerous modifications and variations could be made thereto by those skilled in the art without departing from the scope of the invention set forth in the claims.

What is claimed is:

1. An implantable sensor including a low power rectifier circuit, the low power rectifier circuit comprising:
   a hermetically sealed case;
   a pair of external input lines on which a pulsed power signal is received into said case;
   a pair of output lines on which an operating voltage is made available;
   N-MOS and P-MOS field effect transistor (FET) switches inside said case that automatically connect an appropriate one of the pair of input lines to an appropriate one of the pair of output lines in synchrony with positive and negative pulses of the pulsed power signal; and
   a filter capacitor inside said case connected between the pair of output lines,
   wherein a data signal on the pair of external input lines supplies power to the circuit.

2. The implantable sensor including the low power rectifier circuit of claim 1, further comprising a pulsed power signal source arranged outside said case, wherein said pulsed power signal source operates by inductive coupling of a high frequency AC signal to generate the pulsed power signal on said input lines.

3. The implantable sensor including the low power rectifier circuit of claim 1 wherein the N-MOS and P-MOS FET switches comprise:
   a first P-MOS FET that, when turned on, connects a first one of the input lines to a first one of the output lines;
   a second P-MOS FET that, when turned on, connects a second one of the input lines to the first one of the output lines;
   a first N-MOS FET that, when turned on, connects the first one of the input lines to a second one of the output lines;

a second N-MOS FET that, when turned on, connects the second one of the input lines to the second one of the output lines; and a detector circuit that, when there is a positive pulse within the pulsed power signal on the first one of the input lines relative to the second one of the input lines, turns the first P-MOS FET on, the second N-MOS FET on, and maintains the second P-MOS off, and the first N-MOS FET off; and, when there is a negative pulse within the pulsed power signal on the first one of the input lines relative to the second one of the input lines, turns the second P-MOS FET on, the first N-MOS FET on, and maintains the first P-MOS FET off, and the second N-MOS FET off.

4. The implantable sensor including the low power rectifier circuit of claim 3 wherein the detector circuit comprises:

a first detector circuit that in response to a positive pulse within the pulsed power signal on the first one of the input lines relative to the second one of the input lines exceeding a first threshold value turns on the first P-MOS FET, and that in response to a negative pulse within the pulsed power signal on the first one of the input lines relative to the second one of the input lines exceeding a second threshold value turns on the first N-MOS FET; and a second detector circuit that in response to a positive pulse within the pulsed power signal on the second one of the input lines relative to the first one of the input lines exceeding the first threshold value turns on the second P-MOS FET, and that in response to a negative pulse within the pulsed power signal on the second one of the input lines relative to the first one of the input lines exceeding the second threshold value turns on the second N-MOS FET.

5. The implantable sensor including the low power rectifier circuit of claim 3 wherein the detector circuit comprises:

a first detector circuit that turns the first P-MOS FET on only when there is a positive pulse within the pulsed power signal on the first one of the input lines relative to the second one of the input lines that has an amplitude exceeding a first threshold value;

a second detector circuit that turns the second P-MOS FET on only when there is a positive pulse within the pulsed power signal on the second one of the input lines relative to the first one of the input lines that has an amplitude exceeding the first threshold value;

a third detector circuit that turns the first N-MOS FET on only when there is a negative pulse within the pulsed power signal on the first one of the input lines relative to the second one of the input lines that has a negative amplitude exceeding a second threshold value; and a fourth detector circuit that turns the second N-MOS FET on only when there is a negative pulse within the pulsed power signal on the second one of the input lines relative to the first one of the input lines that has a negative amplitude exceeding the second threshold value.

6. The implantable sensor including the low power rectifier circuit of claim 5 wherein all of the first, second, third and fourth switches and respective detector circuits are part of a single integrated circuit.

7. The implantable sensor including the low power rectifier circuit of claim 5 wherein each of the first, second, third and fourth detector circuits include a complementary N-MOS and P-MOS transistor pair connected as a detector circuit to be biased ON only when a pulse of the pulsed power signal present on the pair of input lines has an amplitude greater than a bias reference voltage.

8. The implantable sensor including the low power rectifier circuit of claim 7 wherein the complementary N-MOS and P-MOS transistor pair of each detector circuit has a first bias reference voltage connected to a gate terminal of its P-MOS transistor, and a second bias reference voltage connected to a gate terminal of its N-MOS transistor.

9. The implantable sensor including the low power rectifier circuit of claim 8 further including a bias generator circuit that generates the first and second reference voltages, and wherein the bias generator circuit includes circuitry for dynamically setting the first and second reference voltages to an operational level when a power signal is present on the pair of input lines, and to a low power standby level when a power signal is not present on the pair of input lines.

10. The implantable sensor including the low power rectifier circuit of claim 9 wherein the bias generator circuit generates a first bias signal that is a fixed amount less than the voltage present on the filter capacitor as sensed on the first voltage rail, and wherein the first detector circuit closes the first switch to connect the first input line to the first voltage rail only when the incoming voltage signal on the first input line exceeds the first bias signal.

11. The implantable sensor including the low power rectifier circuit of claim 10 wherein the second detector circuit closes the second switch to connect the second input line to the first voltage rail only when the incoming voltage signal of the first input line relative to the second input line is a positive voltage greater than the first bias signal.

12. The implantable sensor including the low power rectifier circuit of claim 11 wherein the bias generator circuit includes circuitry for dynamically changing the first bias signal from a first value to a second value whenever an incoming voltage signal is present on the first input line relative to the second input line.

13. The implantable sensor including the low power rectifier circuit of claim 9 wherein the bias generator circuit generates a second bias signal that is a fixed amount smaller than a negative voltage present on the filter capacitor as sensed at the second voltage rail relative to the first voltage rail, and wherein the third detector circuit closes the third switch to connect the first input line to the second voltage rail only when the incoming voltage signal on the first input line relative to the second voltage line is a negative voltage greater than the second bias signal.

14. The implantable sensor including the low power rectifier circuit of claim 13 wherein the fourth detector circuit closes the fourth switch to connect the second input line to the second voltage rail only when the incoming voltage signal on the second input line relative to the first input line is a negative voltage greater than the second bias signal.

15. The implantable sensor including the low power rectifier circuit of claim 14 wherein the bias generator circuit includes circuitry for dynamically changing the second bias signal from a first value to a second value whenever an incoming voltage signal is present on the second input line relative to the first input line.

16. The implantable sensor including the low power rectifier circuit of claim 8 further including a complementary N-MOS and P-MOS inverter circuit interposed between each detector circuit and the respective first/second P-MOS/N-MOS FET switch controlled by the detector circuit.

17. The implantable sensor including the low power rectifier circuit of claim 1 further including a startup voltage source for providing a voltage to the filter capacitor connected between the pair of output lines at a time when no operating voltage is present on said filter capacitor.

18. The implantable sensor including the low power rectifier circuit of claim 17 wherein the startup voltage source comprises parasitic diodes within the N-MOS FET switches, and parasitic PNP bipolar transistors within the P-MOS FET switches, which parasitic diodes and transistors are sufficiently forward biased by an initial power signal on the pair of input lines to cause an initial operating voltage derived from the initial power signal to be stored on said filter capacitor.

19. The implantable sensor including the low power rectifier circuit of claim 1 wherein the pulsed power signal comprises a pulse train of biphasic pulses, each biphasic pulse of the pulse train having a negative pulse and a positive pulse.

20. The implantable sensor including the low power rectifier circuit of claim 19 wherein the frequency of the biphasic pulses in the pulse train ranges from 10 to 500,000 biphasic pulses per second, and wherein each positive and negative pulse within each biphasic pulse has a pulse width of between about 1 to 3 microseconds.

21. The implantable sensor including the low power rectifier circuit of claim 1 further including:
a sensor circuit that derives its operating power from the filter capacitor; and is enclosed in the hermetically sealed case.

22. The implantable sensor including the low power rectifier circuit of claim 1,
wherein the low power rectifier circuit is a low power switched rectifier circuit;
wherein a first one of the pair of output lines comprises a first voltage rail and a second one of the pair of output lines comprises a second voltage rail;
wherein the filter capacitor is a storage capacitor connected between the first and second voltage rails;
wherein the pair of external input lines comprises first and second input lines;
wherein the N-MOS and P-MOS FET switches comprise:
a first switch connecting the first input line to the first voltage rail;
a second switch connecting the second input line to the first voltage rail;
a third switch connecting the first input line to the second voltage rail; and
a fourth switch connecting the second input line to the second voltage rail;
wherein the low power switched rectifier circuit further comprises:
a detector circuit for each of said first, second, third and fourth switches, respectively, powered by voltage on the storage capacitor, that automatically controls its respective switch to close and open as a function of the voltage signal appearing on the first input line relative to the second input line such that, in concert, the first and fourth switches close and the second and third switches open in response to a positive signal on the first input line relative to the second input line, and such that second and third switches close and the first and fourth switches open in response to a negative signal on the first input line relative to the second input line, whereby the first input line is automatically connected to the first voltage rail and the second input line is automatically connected to the second voltage rail whenever a positive signal appears on the first input line relative to the second input line, and whereby the first input line is automatically connected to the second voltage rail and the second input line is automatically connected to the first voltage rail whenever a negative signal appears on the first input line relative to the second input line; and a startup voltage source for supplying the storage capacitor with an initial voltage sufficient to power each of the detector circuits;
wherein a data signal on the first and second input lines supplies power to the circuit.

23. The implantable sensor including the low power switched rectifier circuit of claim 22, wherein the data signal is biphasic.

24. The implantable sensor including the low power switched rectifier circuit of claim 22 further including:
a sensor circuit that derives its operating power from the storage capacitor;
wherein the hermetically sealed case encloses the low power switched rectifier circuit and the sensor circuit;
whereby the sealed case containing the sensor circuit and low power rectifier circuit may be implanted within living tissue.

25. The implantable sensor including the low power rectifier circuit of claim 1, further comprising a sensor circuit that derives its operating power from the filter capacitor, wherein the sensor circuit comprises a low power current-to-frequency (I/F) converter circuit for use within an implantable device, the low power I/F converter circuit comprising:
an amplifier having two input terminals and an output terminal, the amplifier for differentially amplifying an electrical signal applied between its two input terminals to provide an amplified output signal appearing on its output terminal;
a first capacitor electrically connected between a first input terminal of the amplifier and a low reference voltage;
a voltage controlled oscillator (VCO) circuit having a voltage-control input terminal and a VCO output terminal, the voltage-control input terminal being connected to the output terminal of the amplifier, the VCO including a generator for generating a frequency output signal $F_{OUT}$ having a frequency that varies as a function of the magnitude of a voltage applied to the voltage-control input; and
a charge-pump circuit coupled to the first capacitor that pumps a discrete charge off of said first capacitor under control of the frequency output signal $F_{OUT}$ generated by the VCO.

26. The implantable sensor including the low power rectifier circuit of claim 25 wherein the amplifier, VCO and charge pump circuit all operate using one supply voltage having a first terminal V+, and a second terminal V− and wherein the low reference voltage is the voltage on a second input terminal of the amplifier which is connected to V−.

27. The implantable sensor including the low power rectifier circuit of claim 26 wherein the I/F converter circuit is made up of semiconductor circuit components that consume less than 600 nanoamps (na) of current.

28. The implantable sensor including the low power rectifier circuit of claim 25, wherein the low power I/F converter circuit further includes logic circuits responsive to the $F_{OUT}$ signal to control the charge pump circuit to pump the discrete charge off of the first capacitor at least once during each cycle of the $F_{OUT}$ signal.

29. The implantable sensor including the low power rectifier circuit of claim 28 wherein the discrete charge pumped off of the first capacitor at least once during each cycle of the $F_{OUT}$ signal comprises a charge no greater than about 10 pico coulombs.

30. The implantable sensor including the low power rectifier circuit of claim 29 wherein the logic circuits generate a first clock signal from the $F_{OUT}$ signal having a first phase and a second phase, and wherein the charge pump circuit comprises:
- a generator for generating a reference voltage $V_{REF}$;
- a second capacitor;
- a first set of switches for charging the second capacitor to the reference voltage $V_{REF}$ during the first phase of the first clock signal; and
- a second set of switches for connecting the second capacitor across the first capacitor with opposing polarity during the second phase of the first clock signal;
- whereby the $V_{REF}$ charge that accumulates on the second capacitor during the first phase of the first clock signal is pulled off of the first capacitor during the second phase of the first clock signal.

31. The implantable sensor including the low power rectifier circuit of claim 30 wherein the logic circuits generate a second clock signal from the $F_{OUT}$ signal, and wherein the charge pump circuit further includes:
- a third capacitor;
- a plurality of switches of the second set of switches charges the third capacitor to the reference voltage $V_{REF}$ when the second clock signal goes low; and
- a plurality of switches of the first set of switches connect the third capacitor across the first capacitor with opposing polarity when the second clock signal goes high;
- whereby the $V_{REF}$ charge that accumulates on the third capacitor when the second clock signal goes low is pulled off of the first capacitor when the second clock signal goes high.

32. The implantable sensor including the low power rectifier circuit of claim 1, further comprising a sensor circuit that derives its operating power from the filter capacitor, wherein the sensor circuit comprises an implantable sensor comprising:
- a sensor that generates an analog current as a function of a substance or parameter sensed by the sensor;
- a current-to-frequency (I/F) converter circuit that converts the analog current generated by the sensor to a frequency signal, $F_{OUT}$ having a frequency that varies as a function of the analog current, said I/F converter circuit comprising:
  an amplifier having a positive input terminal, a negative input terminal, and an output terminal, the amplifier for differentially amplifying an electrical signal applied between its two input terminals to provide an amplified output signal that appears on its output terminal;
  a first capacitor connected between a first input terminal of the amplifier and a low reference voltage;
  a voltage controlled oscillator (VCO) circuit having a voltage-control input terminal connected to the output terminal of the amplifier, and a VCO output terminal, the VCO including a generator for generating the frequency signal $F_{OUT}$ as an output signal of the VCO, the signal $F_{OUT}$ having a frequency that varies as a function of the magnitude of a voltage applied to the voltage-control input;
  a charge-pump circuit coupled to the first capacitor that pumps a discrete charge off of the first capacitor under control of the frequency of the signal $F_{OUT}$; and
  wherein an analog electrical current from the sensor applied to the first capacitor tends to cause a charge to accumulate on the first capacitor as a function of the magnitude of the electrical current, which charge tends to increase the output voltage of the amplifier so as to increase the frequency of the signal $F_{OUT}$ which increased frequency causes charge to be pumped off of the first capacitor at an increased rate, wherein the amplifier forces the frequency of the $F_{OUT}$ signal to whatever rate is needed to maintain the charge on the first capacitor at essentially zero, whereby the frequency of the VCO signal varies as a function of the magnitude of the analog electrical current applied to the first capacitor.

33. The implantable sensor including the low power rectifier circuit of claim 32 wherein the amplifier, VCO and charge pump circuit all operate using one supply voltage having a first terminal V+, and a second terminal V−, and wherein the low reference voltage is the voltage on a second input terminal of the amplifier which is connected to V−.

34. The implantable sensor including the low power rectifier circuit of claim 33 wherein the implantable sensor further includes a logic circuitry responsive to the frequency signal $F_{OUT}$ generated by the VCO to control the charge pump circuit to pump the discrete charge off of the first capacitor at least once during each cycle of the $F_{OUT}$ signal.

35. The implantable sensor including the low power rectifier circuit of claim 34 wherein the discrete charge pumped off of the first capacitor at least once during each cycle of the $F_{OUT}$ signal comprises a charge no greater than about 10 pico-coulombs.

36. The implantable sensor including the low power rectifier circuit of claim 32 wherein the current-to-frequency converter is within the hermetically sealed part of said implantable sensor which comprises a hermetically sealed part and a non-hermetically sealed part, with electrical feedthroughs providing electrical connections between said hermetically sealed part and said non-hermetically sealed part.

37. The implantable sensor including the low power rectifier circuit as in claim 1, further comprising a sensor circuit that derives its operating power from the filter capacitor, wherein the sensor circuit comprises a low power current-to-frequency converter comprising:
- an amplifier having two input terminals and one output terminal, the amplifier for differentially amplifying an electrical signal applied between its two input terminals to provide an amplified output signal appearing on its output terminal;
- a first capacitor connected between a first input terminal of the amplifier and a low reference voltage;
- a voltage controlled oscillator (VCO) circuit having a voltage-control input terminal and a VCO output terminal, the voltage-control input terminal being connected to the output terminal of the amplifier, the VCO including a generator for generating a VCO signal having a frequency that varies as a function of the magnitude of a voltage applied to the voltage-control input;
- a charge-pump circuit coupled to the first capacitor of the amplifier for pumping a discrete charge off of said first capacitor under control of the frequency of said VCO signal; and
- wherein an electrical current applied to the first capacitor tends to cause a charge to accumulate on the first capacitor as a function of the magnitude of the electrical current, which charge tends to increase the output voltage of the amplifier so as to increase the frequency of the VCO signal, which increased VCO frequency causes the charge to be pumped off of the first capacitor at an increased rate, wherein the amplifier forces the frequency of the VCO signal to whatever rate is needed to maintain the charge on the first capacitor at essentially zero, whereby the frequency of the VCO signal varies as a function of the magnitude of the electrical current applied to the first capacitor.

38. The implantable sensor including the low power rectifier circuit of claim 37 wherein the amplifier, VCO and charge pump circuit all operate using one supply voltage having a first terminal V+, and a second terminal V−, and wherein the low reference voltage is the voltage on a second input terminal of the amplifier which is connected to V−.

39. The implantable sensor including the low power rectifier circuit of claim 37 wherein the current-to-frequency converter consumes less than about 600 nanoamps (na) of current.

40. The implantable sensor including the low power rectifier circuit of claim 37 wherein the low power current-to-frequency converter further includes a latch logic circuit coupled to the VCO for generating a clock signal for controlling the charge pump circuit to pump the discrete charge off of the first capacitor at least once during each cycle of the clock signal.

41. The implantable sensor including the low power rectifier circuit of claim 40 wherein the discrete charge pumped off of the first capacitor at least once during each cycle of the clock signal comprises a charge no greater than about 10 pico-coulombs.

42. The implantable sensor including the low power rectifier circuit of claim 40 wherein the first clock signal has a first phase and a second phase, and wherein the charge pump circuit comprises:
  a second capacitor;
  a first set of switches for charging the second capacitor to a reference voltage $V_{REF}$ during the first phase of the first clock signal;
  a second set of switches for connecting the second capacitor across the first capacitor with opposing polarity during the second phase of the first clock signal; and
  whereby the $V_{REF}$ charge that accumulates on the second capacitor during the first phase of the first clock signal is pulled off of the first capacitor during the second phase of the first clock signal.

43. The implantable sensor including the low power rectifier circuit of claim 42 wherein the latch logic circuit coupled to the VCO also generates a second clock signal, and wherein the charge pump circuit further includes:
  a third capacitor;
  a plurality of switches of the second set of switches charges the third capacitor to the reference voltage $V_{REF}$ when the second clock signal goes low; and
  a plurality of switches of the first set of switches connect the third capacitor across the first capacitor with opposing polarity when the second clock signal goes high;
  whereby the $V_{REF}$ charge that accumulates on the third capacitor when the second clock signal goes low is pulled off of the first capacitor when the second clock signal goes high.

44. The implantable sensor including the low power rectifier circuit of claim 37 wherein the low power current-to-frequency converter is within the hermetically sealed part of said medical device which comprises a hermetically sealed part and a non-hermetically sealed part, with electrical feedthroughs providing electrical connections between said hermetically sealed part and said non-hermetically sealed part.

45. The implantable sensor including the low power rectifier circuit of claim 1, further comprising a sensor circuit that derives its operating power from the filter capacitor, wherein the sensor circuit comprises a very low power current-to-frequency (I/F) converter circuit for use within an implantable device, the I/F converter circuit comprising:
  an amplifier having two input terminals and an output terminal, the amplifier for differentially amplifying an electrical signal applied between its two input terminals to provide an amplified output signal appearing on its output terminal;
  a first capacitor electrically connected between a first input terminal of the amplifier and a low reference voltage;
  a voltage controlled oscillator (VCO) circuit having a voltage-control input terminal and a VCO output terminal, the voltage control input terminal being connected to the output terminal of the amplifier, the VCO including a generator for generating a frequency output signal $F_{OUT}$, having a frequency that varies as a function of the magnitude of a voltage applied to the voltage control input;
  a charge-pump circuit coupled to the first capacitor that pumps a discrete charge off of said first, capacitor under control of the frequency output signal $F_{OUT}$ generated by the VCO;
  logic circuits responsive to the $F_{OUT}$ signal to control the charge pump circuit to pump the discrete charge off of the first capacitor at least once during each cycle of the $F_{OUT}$ signals;
  said converter circuit wherein the discrete charge pumped off of the first capacitor at lease once during each cycle of the $F_{OUT}$ signal comprises a charge no greater than about 10 picocoulombs;
  said I/F converter circuit wherein the logic circuits generate a first clock signal from the $F_{OUT}$ signal having a first phase and a second phase and a second clock signal from the $F_{OUT}$ signal, and wherein the charge pump circuit comprises a generator for generating a reference voltage $V_{REF}$;
  a second capacitor;
  a first set of switches for charging the second capacitor to the reference voltage $V_{REF}$ during the first phase of the first clock signal;
  a second set of switches for connecting the second capacitor across the first capacitor with opposing polarity during the second phase of the first clock signal;
  whereby the $V_{REF}$ charge that accumulates on the second capacitor during the first phase of the first clock signal is pulled off of the first capacitor during the second phase of the first clock signal;
  wherein the charge pump circuit further includes:
  a third capacitor;
  a plurality of switches of the second set of switches charges the third capacitor to the reference voltage $V_{REF}$ when the second clock signal goes low; and
  a plurality of switches of the first set of switches connect the third capacitor across the first capacitor with opposing polarity when the second clock signal goes high;
  whereby the $V_{REF}$ charge that accumulates on the third capacitor when the second clock signal goes low is pulled off of the first capacitor when the second clock signal goes high.

46. The implantable sensor including the low power rectifier circuit of claim 45 wherein the charge pump circuit pumps the discrete charge off of the first capacitor at least twice during each cycle of the $F_{OUT}$ signal.

47. The implantable sensor including the low power rectifier circuit of claim 45 wherein the charge pump circuit comprises two capacitors that alternately pump the discrete charge off of the first capacitor.

48. The implantable sensor including the low power rectifier circuit of claim 45 wherein the charge pump circuit comprises:

a circuit that generates a clock signal with a first phase and a second phase from the $F_{OUT}$ signal;
a generator for generating a reference voltage $V_{REF}$;
a second capacitor;
a third capacitor;
wherein during the first phase of the clock signal the second capacitor is charged to the reference voltage $V_{REF}$ and wherein during the second phase of the clock signal the third capacitor is charge to the reference voltage $V_{REF}$; and
wherein during the second phase of the clock signal the $V_{REF}$ charge that accumulated on the second capacitor during the first phase of the clock signal is pulled off of the first capacitor and wherein during the first phase of the clock signal the $V_{REF}$ charge that accumulated on the third capacitor during the second phase of the clock signal is pulled off of the first capacitor.

49. The implantable sensor including the low power rectifier circuit of claim 45 wherein the charge pump circuit comprises:
a circuit that generates two non-overlapping clock signals $CLK_A$ and $CLK_B$ from the $F_{OUT}$ signal;
a generator for generating a reference voltage $V_{REF}$;
a second capacitor;
a third capacitor;
wherein when $CLK_A$ goes high the second capacitor is charged to the reference voltage $V_{REF}$ and wherein when $CLK_B$ goes high the third capacitor is charged to the reference voltage $V_{REF}$; and
wherein when $CLK_B$ goes high the $V_{REF}$ charge that accumulated on the second capacitor is pulled off of the first capacitor and wherein when $CLK_A$ goes high the $V_{REF}$ charge that accumulated on the third capacitor is pulled off of the first capacitor.

50. The implantable sensor including the low power rectifier circuit of claim 1, wherein
the rectifier circuit is for rectifying the received pulsed power signal and for generating the operating voltage therefrom; and
electronic circuits within said hermetically sealed case and powered by said operating voltage for performing a specified function.

51. The implantable sensor including the low power rectifier circuit of claim 50 wherein the N-MOS and P-MOS FET switches comprise:
a first P-MOS FET that, when turned on, connects a first one of the input lines to a first one of the output lines;
a second P-MOS FET that, when turned on, connects a second one of the input lines to the first one of the output lines;
a first N-MOS FET that, when turned on, connects the first one of the input lines to a second one of the output lines;
a second N-MOS FET that, when turned on, connects the second one of the input lines to the second one of the output lines;
a first detector circuit that turns the first P-MOS FET switch on only when the power signal on the first one of the input lines relative to the second one of the input lines has a positive amplitude exceeding a first threshold value;
a second detector circuit that turns the second P-MOS FET switch on only when the power signal on the second one of the input lines relative to the first one of the input lines has a positive amplitude exceeding the first threshold value;
a third detector circuit that turns the first N-MOS FET switch on only when the power signal on the first one of the input lines relative to the second one of the input lines has a negative amplitude exceeding a second threshold value; and
a fourth detector circuit that turns the second N-MOS FET switch on only when the power signal on the second one of the input lines relative to the first one of the input lines has a negative amplitude exceeding the second threshold value.

52. The implantable sensor including the low power rectifier circuit of claim 51 wherein each of the first, second, third and fourth detector circuits include a complementary N-MOS and P-MOS transistor pair connected as a detector circuit to be biased ON only when a power signal greater than a bias reference voltage is present on the pair of input lines.

53. The implantable sensor including the low power rectifier circuit of claim 52 wherein the complementary N-MOS and P-MOS transistor pair of each detector circuit has a first bias reference voltage connected to a gate terminal of its P-MOS transistor, and a second bias reference voltage connected to a gate terminal of its N-MOS transistor.

54. The implantable sensor including the low power rectifier circuit of claim 53 further including a bias generator circuit that generates the first and second reference voltages, and wherein the bias generator circuit includes circuitry for dynamically setting the first and second reference voltages to an operational level when a power signal is present on the pair of input lines and to a low power standby level when a power signal is not present on the pair of input lines.

55. The implantable sensor including the low power rectifier circuit of claim 52 further including a complementary N-MOS and P-MOS inverter circuit interposed between each detector circuit and the respective first/second P-MOS/N-MOS FET switch controlled by the detector circuit.

56. The implantable sensor including the low power rectifier circuit of claim 50 further including a startup voltage source for providing a voltage to the filter capacitor connected between the pair of output lines at a time when no operating voltage is present on said filter capacitor.

57. The implantable sensor including the low power rectifier circuit of claim 56 wherein the startup voltage source comprises parasitic diodes within the N-MOS FET switches, and parasitic PNP bipolar transistors within the P-MOS FET switches, which parasitic diodes and transistors are sufficiently forward biased by an initial power signal on the pair of input lines to cause an initial operating voltage derived from the initial power signal to be stored on said filter capacitor.

58. The implantable sensor including the low power rectifier circuit of claim 50, wherein said electronic circuits comprise:
a sensor circuit that is adapted to receive and transmit data on said pair of external input lines, the data signal also being said power signal.

59. The implantable sensor including the low power rectifier circuit of claim 58, wherein said sensor circuit includes a hermetically sealed portion and a non-hermetically sealed portion, wherein said non-hermetically sealed portion has at least one electrode associated therewith, said hermetically sealed portion of the sensor circuit comprising means for measuring a specified parameter within body fluids or tissue to which said at least one electrode is exposed, and means for performing at least one integrity test to verify proper operation of said sensor circuit.

60. An implantable sensor including a low power rectifier circuit, the low power rectifier circuit comprising:
a pair of input lines on which a pulsed power signal is received;

a pair of output lines on which an operating voltage is made available;

N-MOS and P-MOS field effect transistor (FET) switches that automatically connect an appropriate one of the pair of input lines to an appropriate one of the pair of output lines in synchrony with positive and negative pulses of the pulsed power signal; and a filter capacitor connected between the pair of output lines;

wherein a data signal on the pair of input lines supplies power to the circuit.

61. The implantable sensor including the low power rectifier circuit of claim 60, wherein the data signal is biphasic.

* * * * *